United States Patent
Nakagawa et al.

(10) Patent No.: US 9,974,849 B2
(45) Date of Patent: May 22, 2018

(54) HUMAN PAPILLOMA VIRUS THERAPEUTIC VACCINE

(71) Applicant: The Board of Trustees of the University of Arkansas, Little Rock, AR (US)

(72) Inventors: Mayumi Nakagawa, Little Rock, CA (US); Byeong S. Chang, Thousand Oaks, CA (US)

(73) Assignee: Bioventures, LLC, Little Rock, AR (US)

( * ) Notice: Subject to any disclaimer, the term of this patent is extended or adjusted under 35 U.S.C. 154(b) by 0 days. days.

(21) Appl. No.: 15/028,760

(22) PCT Filed: Oct. 11, 2014

(86) PCT No.: PCT/US2014/060198
§ 371 (c)(1),
(2) Date: Apr. 12, 2016

(87) PCT Pub. No.: WO2015/054678
PCT Pub. Date: Apr. 16, 2015

(65) Prior Publication Data
US 2016/0250315 A1 Sep. 1, 2016

Related U.S. Application Data

(60) Provisional application No. 61/890,306, filed on Oct. 13, 2013.

(51) Int. Cl.

| | | |
|---|---|---|
| *C07K 14/025* | (2006.01) | |
| *C07K 7/00* | (2006.01) | |
| *A61K 39/12* | (2006.01) | |
| *A61K 39/39* | (2006.01) | |
| *A61K 9/00* | (2006.01) | |
| *A61K 47/18* | (2017.01) | |
| *A61K 47/26* | (2006.01) | |
| *C12N 7/00* | (2006.01) | |
| *A61K 39/00* | (2006.01) | |
| *A61K 9/19* | (2006.01) | |

(52) U.S. Cl.
CPC ............ *A61K 39/12* (2013.01); *A61K 9/0021* (2013.01); *A61K 39/39* (2013.01); *A61K 47/183* (2013.01); *A61K 47/26* (2013.01); *C12N 7/00* (2013.01); *A61K 9/19* (2013.01); *A61K 2039/55588* (2013.01); *A61K 2039/585* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | |
|---|---|---|
| 2009/0088377 A1 | 4/2009 | Quraishi |
| 2009/0136531 A1* | 5/2009 | Nakagawa ........... C07K 14/005 424/186.1 |
| 2011/0293651 A1 | 12/2011 | Nakagawa |

OTHER PUBLICATIONS van den Hende et al. Skin reactions to human papillomavirus (HPV) 16 specific antigens intradermally injected in healthy subjects and patients with cervical neoplasia. Int. J. Cancer: 123, 146-152 (2008).*
Welters et al. Frequent Display of Human Papillomavirus Type 16 E6-specific Memory T-Helper Cells in the Healthy Population as Witness of Previous Viral Encounter. Cancer Research 63, 636-641, Feb. 1, 2003.*
GenBank: AAL01351.1 . E6 protein, partial [Human papillomavirus type 16]. Dated Oct. 9, 2003.*
van der Burg et al. Identification of a Conserved Universal Th Epitope in HIV-1 Reverse Transcriptase That Is Processed and Presented to HIV-Specific CD4+ T Cells by at Least Four Unrelated HLA-DR Molecules. J Immunol Jan. 1, 1999, 162 (1) 152-160.*
Malavolta et al. Interpretation of the dissolution of insoluble peptide sequences based on the acid-base properties of the solvent. Protein Science (2006), 15:1476-1488.*
Walker et al. Using protein-based motifs to stabilize peptides. J Pept Res. Nov. 2003;62(5):214-26.*

* cited by examiner

Primary Examiner — Nianxiang Zou
(74) Attorney, Agent, or Firm — Hugh McTavish

(57) ABSTRACT

Peptides and compositions for a therapeutic vaccine to treat persons infected with human papilloma virus are presented. Methods of using the compositions and treating persons infected with human papilloma virus, including those at risk of cancer or already with cancer from human papilloma virus, are presented.

15 Claims, 15 Drawing Sheets

SEQUENCE LISTING

<160> NUMBER OF SEQ ID NOS: 5

<210> SEQ ID NO 1
<211> LENGTH: 158
<212> TYPE: PRT
<213> ORGANISM: Human papillomavirus type 16

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 2
<211> LENGTH: 45
<212> TYPE: PRT
<213> ORGANISM: Human papillomavirus type 16

<400> SEQUENCE: 2

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu
        35                  40                  45

<210> SEQ ID NO 3
<211> LENGTH: 35
<212> TYPE: PRT
<213> ORGANISM: Human papillomavirus type 16

<400> SEQUENCE: 3

Arg Arg Glu Val Tyr Asp Phe Ala Phe Arg Asp Leu Cys Ile Val Tyr
1               5                   10                  15

Arg Asp Gly Asn Pro Tyr Ala Val Cys Asp Lys Cys Leu Lys Phe Tyr
            20                  25                  30

Ser Lys Ile
        35

<210> SEQ ID NO 4
<211> LENGTH: 35
<212> TYPE: PRT
<213> ORGANISM: Human papillomavirus type 16

-continued

```
<400> SEQUENCE: 4

Ser Glu Tyr Arg His Tyr Cys Tyr Ser Leu Tyr Gly Thr Thr Leu Glu
1               5                   10                  15

Gln Gln Tyr Asn Lys Pro Leu Cys Asp Leu Leu Ile Arg Cys Ile Asn
            20                  25                  30

Cys Gln Lys
        35

<210> SEQ ID NO 5
<211> LENGTH: 43
<212> TYPE: PRT
<213> ORGANISM: Human papillomavirus type 16

<400> SEQUENCE: 5

Pro Leu Cys Pro Glu Glu Lys Gln Arg His Leu Asp Lys Lys Gln Arg
1               5                   10                  15

Phe His Asn Ile Arg Gly Arg Trp Thr Gly Arg Cys Met Ser Cys Cys
            20                  25                  30

Arg Ser Ser Arg Thr Arg Arg Glu Thr Gln Leu
        35                  40
```

HUMAN PAPILLOMA VIRUS THERAPEUTIC VACCINE

This invention was made with government support under grant number CA-143130 A1 awarded by the National Institutes of Health. The government has certain rights in the invention.

BACKGROUND OF THE INVENTION

Cervical cancer is the fourth most common cancer in women worldwide, with an annual incidence of 528,000 cases and mortality of 266,000 cases. Every year in the United States, there are 12,360 new cases of cervical cancer and 4,020 deaths. High-risk Human Papilloma virus, the most common type being HPV16, is the major cause of cervical cancer. Among the over one hundred different types of Human Papilloma virus, at least 15 are strongly associated with invasive squamous cell cancer of the cervix. HPV16 is the one most commonly found associated with this cancer.

Human Papilloma virus infection is also associated with the precursor lesion of cervical cancer, squamous intraepithelial lesion. While most low-grade squamous intraepithelial lesions prospectively regress spontaneously, some progress to high-grade squamous intraepithelial lesions. These high-grade lesions, in particular, cervical intraepithelial neoplasia-3 are associated with a high rate progression to invasive cervical cancer.

Two early gene products, E6 and E7, mediate transformation to a malignant phenotype by Human Papilloma virus. Both of these viral proteins have been shown to interact with the products of cellular human tumor suppressor genes. The E6 protein can bind and promote degradation of cell-encoded p53, while the E7 protein interacts with the retinoblastoma susceptibility gene product. Constitutive expression of HPV E6/E7 proteins is required for the maintenance of a malignant phenotype of cervical cancer.

Cell-mediated immunity plays an important role in controlling Human Papilloma virus infection and Human Papilloma virus-associated diseases. CD4 T cells are important in the development of anti-tumor responses. It is believed that the effectiveness of these CD4 T cells lies in their ability to deliver help for priming and maintaining CD8 cytotoxic T lymphocytes, which are thought to serve as the dominant effector cells in tumor elimination. Immunohistochemical analyses of squamous intraepithelial lesions and cervical cancer specimens have demonstrated the presence of activated cytotoxic T lymphocytes in lesions. The CD4 T cells activate cytotoxic T lymphocytes by producing T helper 1 cytokines and by providing activation signals for priming of tumor-specific cytotoxic T lymphocytes to professional antigen presenting cells. CD8-positive cytotoxic T lymphocytes recognize foreign peptides that are 8 to 11 amino acids in length and bound to and presented by Human Leukocyte Antigen class I molecules. These peptides are called T cell epitopes.

Memory T cells play an important role in maintaining long-term immunity to previously encountered pathogens or tumor antigens. They may proliferate, and rapidly acquire effector functions to kill virus-infected cells or tumor cells, and secrete cytokines that inhibit replication of the pathogen after re-stimulation with re-exposure to antigen. Antigen presenting cells, which may transfer peripheral antigenic signals to the lymphoid organs, play a crucial role in the induction of antigen-specific T cell immunity responses to Human Papilloma virus infection and Human Papilloma virus-associated tumors. Dendritic cells as professional antigen presenting cells express high level of major histocompatibility complex and co-stimulatory molecules. Insufficient or improper activation of dendritic cells, caused by lack of pro-inflammatory signal, leading to antigen presentation not in an appropriate co-stimulatory context is one reason for the failure of antitumor immunity.

Prophylactic HPV vaccines are available, and work by preventing HPV infection. But they are not effective in individuals who are already infected. An HPV therapeutic vaccine would benefit women who have pre-cancerous lesions but wish to have children since standard surgical treatments are associated with increased risk for pre-term delivery. It would also benefit women and men who live in developing regions of the world and do not have access to surgical modalities.

SUMMARY

Pharmaceutical formulations containing HPV peptides for use as therapeutic vaccines are provided. Also provided is a method of making the formulations, especially a method of solubilizing a difficult-to-solubilize HPV peptide. Also provided are methods of treating HPV infection and HPV-associated lesions, including HPV-associated cancers.

One embodiment provides a method to solubilize an HPV E6 peptide comprising: solubilizing an HPV E6 peptide A of 20 to 100 amino acids in length and comprising at least 20 consecutive residues of HPV E6 81-115 (residues 81-115 of SEQ ID NO:1) in a buffer that before the step of solubilizing the HPV peptide A contains in dissolved form two or more HPV peptides Y of 10 to 100 amino acids in length each that collectively comprise at least 50% of the sequence of HPV E6 1-80 (residues 1-80 of SEQ ID NO:1) and at least 50% of HPV E6 116-158 (residues 116-158 of SEQ ID NO:1) to create a final soluble composition containing the peptide A in dissolved form and the peptides Y in dissolved form. The peptides Y in the buffer before the step of solubilizing the peptide A are preferably in fully dissolved form (no insoluble peptides Y) and in the final soluble composition the peptides A and Y are preferably in fully dissolved form.

Another embodiment provides a pharmaceutical formulation comprising: (a) one or more HPV E6 peptides, each of a length of 10-100 amino acid residues; (b) glutamate at a concentration of 2-40 mM; (c) trehalose at a concentration of 0.3% to 5% w/v; (d) glycine at a concentration of 0.2% to 10% w/v; wherein the formulation is at a pH of 3.0 to 5.0.

Another embodiment provides a pharmaceutical formulation comprising: an HPV E6 peptide A and one or more HPV peptides Y, the composition made by a method comprising: solubilizing an HPV E6 peptide A of 20 to 100 amino acids in length and comprising at least 20 consecutive residues of HPV E6 81-115 (residues 81-115 of SEQ ID NO:1) in a buffer that before the step of solubilizing the HPV peptide A contains in dissolved form two or more HPV peptides Y of 10 to 100 amino acids in length each that collectively comprise at least 50% of the sequence of HPV E6 1-80 (residues 1-80 of SEQ ID NO:1) and at least 50% of HPV E6 116-158 (residues 116-158 of SEQ ID NO:1) to create a final soluble composition containing the peptide A in dissolved form and the peptides Y in dissolved form.

Another embodiment provides a method of decreasing infection from human papilloma virus (HPV) in an individual or increasing regression of HPV-associated lesions in an HPV-positive individual, comprising: administering a pharmaceutical formulation comprising (a) one or more HPV E6 peptides, each of a length of 10-100 amino acid residues; (b) glutamate at a concentration of 2-40 mM; (c) trehalose at a concentration of 0.3% to 5% w/v; (d) glycine at a concentration of 0.2% to 10% w/v.

It is shown herein in Example 2 that recall antigens, such as CANDIN, enhance the T cell immune response to the HPV peptides tested. A combination of a recall antigen and HPV peptides was contacted with peripheral blood mononuclear cells. Thus, administering a vaccine that includes a recall antigen together with disease-specific antigens may have general applicability to promote a cellular (T cell) immune response to the disease-specific antigens.

Accordingly, one embodiment provides a method of decreasing infection from human papilloma virus (HPV) in an individual or increasing regression of HPV-associated lesions in an HPV-positive individual, to induce a T cell response to HPV, the method comprising: administering to the individual a composition comprising one or more HPV antigens and administering to the individual a recall antigen that is not an HPV antigen; wherein the recall antigen is administered to be in contact with the one or more HPV antigens in the individual; wherein the individual is in need of a T cell response against the one or more HPV antigens; wherein the one or more HPV antigens are not E6 antigens.

In a Phase I clinical trial of patients with women with biopsy-proven high-grade squamous intraepithelial (HSIL), women were treated with intradermal injection of a composition comprising HPV protein E6 residues 1-45 (SEQ ID NO:2), E6 46-80 (SEQ ID NO:3), E6 81-115 (SEQ ID NO:4), and E6 116-158 (SEQ ID NO:5), all mixed with CANDIN as an adjuvant. The dosages tested were 50 ug, 100 ug, and 250 ug of each of the peptides. It was surprisingly found that 4 of 6 subjects (67% in the 50 ug dose group, in 3 of 6 subjects (50%) in the 100 ug does group, and in 0 of 3 subjects in the 250 ug dose group had complete regression of their lesions. In addition, one additional subject in the 50 ug dose group had a partial regression (<0.2 mm2 lesion remaining) This is a surprising result that the lowest dose was the most effective. This is reported in Example 3 below.

Thus, another embodiment provides a unit dosage pharmaceutical composition comprising: 25 to 110 ug of a peptide consisting of SEQ ID NO:2, 25 to 110 ug of a peptide consisting of SEQ ID NO:3, 25 to 110 ug of a peptide consisting of SEQ ID NO:4, 25 to 110 ug of a peptide consisting of SEQ ID NO:5; and a recall antigen; in a unit dosage form for intradermal injection in a volume of 100 to 900 ul.

Another embodiment provides a method of treating HPV infection comprising: injecting into a patient intradermally a unit dosage pharmaceutical composition comprising: 25 to 110 ug of a peptide consisting of SEQ ID NO:2, 25 to 110 ug of a peptide consisting of SEQ ID NO:3, 25 to 110 ug of a peptide consisting of SEQ ID NO:4, 25 to 110 ug of a peptide consisting of SEQ ID NO:5; and a recall antigen; in a unit dosage form for intradermal injection in a volume of 100 to 900 ul.

Another embodiment provides a method of treating a disease caused by microorganism in a mammalian subject comprising: administering intradermally to the subject a composition comprising one or more antigens of the microorganism and administering intradermally to the subject a recall antigen that is not an antigen of the microorganism; wherein the recall antigen is administered to be in contact with the one or more antigens of the microorganism in the subject.

DETAILED DESCRIPTION

Figure 1A:
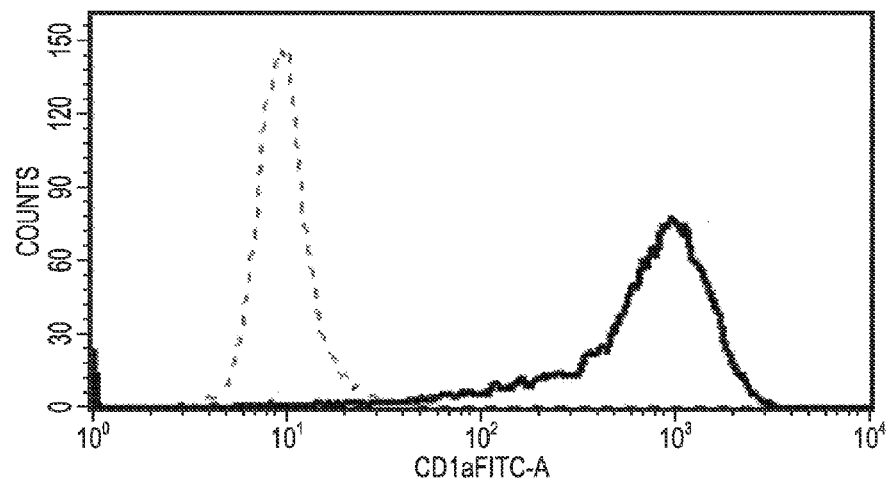
FIGS. 1A-C Surface expressions of CD1a (top), Langerin (middle), and E-cadherin (bottom) show successful conversion to LCs (solid lines). The dotted lines represent the relevant isotype controls.

The invention involves HPV peptides for use in a therapeutic vaccine.

Transformation of squamous epithelium to a malignant phenotype by human papilloma virus is mediated by two early gene products—E6 and E7. Both viral proteins have been shown to interact with the products of cellular human tumor-suppressor genes. The E6 protein can bind and promote degradation of cell-encoded p53, whereas the E7 protein interacts with the retinoblastoma susceptibility gene product. Expressions of E6 and E7 open reading frames have been shown to be necessary and sufficient for the transformation of human cells by HPV-16.

We have investigated previously the epitopes of E6 and E7 that are recognized in favorable immune responses to HPV. (Nakagawa, M. et al., 2010, *Journal of Lower Genital Tract Disease*, Vol. 14, No. 2, p. 124-129; U.S. Patent Publication Nos. 20110293651, 20090136531, 20090117140, 20060182763).

We have identified HPV E6 and E7 peptides for use in therapeutic vaccines, especially HPV E6 peptides (U.S. Patent Publication Nos. 20110293651, 20090136531, 20090117140).

Numerous types of HPV exist. The one most commonly associated with cancer is HPV-16.

The peptides described herein are from the E6 protein of HPV (HPV E6).

The sequence of E6 from HPV-16 is SEQ ID NO:1 below:

```
                                            (SEQ ID NO: 1)
        10          20          30          40
MHQKRTAMFQ  DPQERPRKLP  QLCTELQTTI  HDIILECVYC 50          60          70          80
KQQLLRREVY  DFAFRDLCIV  YRDGNPYAVC  DKCLKFYSKI 90         100         110         120
SEYRHYCYSL  YGTTLEQQYN  KPLCDLLIRC  INCQKPLCPE 130         140         150
EKQRHLDKKQ  RFHNIRGRWT  GRCMSCCRSS  RTRRETQL.
```

The peptides in the following embodiments are HPV E6 peptides, meaning they are derived from the sequence of an HPV E6 protein. The E6 protein can be from any HPV strain. In a preferred embodiment, the peptides are derived from the E6 of HPV-16.

Preferably, the peptides comprise only HPV E6 sequence. But they may comprise other amino acid residues. They may comprise E6 sequence from any HPV strain, not just HPV-16.

The peptides are preferably chemically synthesized, but they may also be produced in a recombinant organism from recombinant DNA technology. They may also be produced by other means known to persons of skill in the art, for instance by proteolysis of E6 or proteolysis of a longer peptide than the peptide produced.

The peptides in some embodiments are acetylated at their amino termini or amidated at their carboxy termini, or both. In other embodiments, neither terminus is modified.

The peptides may be in specific embodiments 10-100, 8-100, 8-75, 8-50, 8-40, 10-75, 10-50, 10-40, 20-100, 20-75, 20-50, 20-40, 30-100, 30-75, 30-50, or 30-40 amino acid residues in length.

The peptides are generally "forward L" meaning that they have the sequence described and the amino acids are L stereoisomers. In specific embodiments, however, the peptides can be reverse D peptides, meaning that the ordinary sequence of amino acid residues is reversed and the amino acids are D stereoisomers.

One embodiment comprises a method to solubilize an HPV E6 peptide comprising: solubilizing an HPV E6 peptide A of 20 to 100 amino acids in length and comprising at least 20 consecutive residues of HPV E6 81-115 (residues 81-115 of SEQ ID NO:1) in a buffer that before the step of solubilizing the HPV peptide A contains in fully dissolved form two or more HPV peptides Y of 10 to 100 amino acids in length each that collectively comprise at least 50% of the sequence of HPV E6 1-80 (residues 1-80 of SEQ ID NO:1) and at least 50% of HPV E6 116-158 (residues 116-158 of SEQ ID NO:1) to create a final soluble composition containing the peptide A in fully dissolved form and the peptides Y in fully dissolved form.

In a specific embodiment, the peptide A is acetylated at its amino terminus and amidated at its carboxyl terminus.

In a specific embodiment, the HPV peptide A comprises residues 81-115 of SEQ ID NO:1. In other embodiments, the HPV peptide A comprises 25 consecutive residues of residues 81-115 of SEQ ID NO:1 or comprises 30 consecutive residues of residues 81-115 of SEQ ID NO:1.

In a specific embodiment, the HPV peptide A consists of residues 81-115 of SEQ ID NO:1.

In specific embodiments, the peptide A is acetylated on its amino terminus and amidated on its carboxyl terminus.

In a specific embodiment, the buffer is at a pH of from about pH 3.0 to about pH 5.0, from about pH 3.5 to about pH 4.5, or from about pH 2.5 to about pH 5.5.

In specific embodiments, the buffer comprises at least 2 mM glutamate. In other embodiments, it may have 2 to 50 mM glutamate, at least 5 mM glutamate, 5 to 50 mM glutamate, or 5 to 25 mM glutamate, or 2 to 25 mM glutamate. The term "glutamate" in this context is intended to include all forms, protonated and unprotonated, of glutamate, i.e., both glutamate and glutamic acid.

In a specific embodiment, the peptides A and Y collectively comprise all of SEQ ID NO:1 or all of an HPV E6 sequence.

In a specific embodiment, peptide A consists of residues 81-115 of SEQ ID NO:1 and the peptides Y are three peptides consisting of residues 1-45, 46-80, and 116-158 of SEQ ID NO:1.

In a more specific embodiment of this, each of the peptides A and Y is acetylated on its amino terminus and amidated on its carboxyl terminus, wherein the buffer is at a pH of from about pH 3.0 to pH 5.0, and after solubilization, peptide A and each of the three peptides Y is at 0.1 to 20 mg/ml concentration. In other embodiments, after solubilization, peptide A and each of the three peptides Y is at 0.1 to 5 mg/ml or 0.02 to 5 mg/ml.

In a specific embodiment, each of the peptides Y is at at least 80% of the weight-to-volume concentration of peptide A in the final soluble composition.

In a specific embodiment, peptide A and each of the peptides Y are at 0.1 to 5 mg/ml in the final soluble composition. In other embodiments, they are at 0.1 to 20 mg/ml, or 0.02 to 5 mg/ml.

One embodiment provides a pharmaceutical composition comprising: (a) one or more HPV E6 peptides, each of a length of 10-100 amino acid residues; (b) glutamate at a concentration of 2-40 mM; (c) trehalose at a concentration of 0.3% to 5% w/v; (d) glycine at a concentration of 0.2% to 10% w/v; wherein the composition has a pH of 3.0 to 5.0.

Other possible ranges of the glutamate concentration are 2 to 20 mM and 5 to 20 mM. Other possible ranges of trehalose concentration are 0.2% to 5% w/v, 0.5% to 5% w/v, and 0.3% to 2% w/v, and 0.5% to 2% w/v. Other possible ranges of glycine concentration are 0.2% or more, 0.3% or more, 0.5% or more, 1% or more, and up to 3%, up to 5%, up to 8%, up to 10%, up to 15%, and up to 20%.

In a specific embodiment, at least one of the one or more HPV E6 peptides comprises residues 46-70 of SEQ ID NO:1 or comprises residues 91-115 of SEQ ID NO:1, or comprises residues 80-88 of SEQ ID NO:1. In a specific embodiment, at least one of the one or more HPV E6 peptides comprises residues 46-70 of SEQ ID NO:1 or comprises residues 91-115 of SEQ ID NO:1.

In a specific embodiment, the pharmaceutical composition comprises at least three HPV E6 peptides each of a length of 10-100 amino acid residues and collectively comprising at least 50% of an HPV E6 sequence.

In specific embodiments, the composition comprises at least one peptide consisting of residues 1-45, 46-80, 81-115, or 116-158 of SEQ ID NO:1; at least two peptides consisting of residues 1-45, 46-80, 81-115, or 116-158 of SEQ ID NO:1; at least three peptides consisting of residues 1-45, 46-80, 81-115, or 116-158 of SEQ ID NO:1, or comprises four peptides consisting respectively of residues 1-45, 46-80, 81-115, and 116-158 of SEQ ID NO:1.

In specific embodiments, each of the peptides is acetylated at its amino terminus and amidated at its carboxy terminus.

The pharmaceutical composition may also comprise a recall antigen. The prototypical recall antigens are those commonly used in immunologic skin testing to test immune response, particularly mumps antigen, *candida* antigen, and *trichophyton* antigen. The test shows if the body "remembers" or "recalls" the antigen, i.e., has a delayed-type hypersensitivity response in the skin where the antigen was administered by intradermal injection.

The term "recall antigen" is defined herein as a substance or mixture containing a plurality of proteinaceous antigens, wherein the mixture induces a delayed-type hypersensitivity response in intradermal skin test in a majority of people previously sensitized or exposed to the recall antigen. The prototypical recall antigens are those commonly used in immunologic skin testing to test immune response, particularly mumps antigen, *candida* antigen, and *trichophyton* antigen. Each of these, although referred to by the singular term "antigen" is actually composed of several or many molecular substances that can induce an immune response.

In specific embodiments, the recall antigen may be mumps antigen (e.g., killed whole mumps virus), *Candida* extract, or *Trichophyton* extract.

In specific embodiments, the recall antigen is killed whole virus, killed whole bacteria, or killed whole microorganisms.

Example 2 below shows that E6 peptides have partial maturation effects on Langerhans cells in vitro, while *Candida* extract was responsible for T cell proliferation in vitro in cells exposed to the E6 peptides. So the *Candida* extract is an excellent adjuvant for the E6 peptides to induce a stronger T cell response to HPV.

We are conducting a clinical trial involving intradermal injection of four HPV E6 peptides together with CANDIN. The peptides are in a pharmaceutical solution A containing 10 mM glutamate, 1.0% w/v trehalose, 2.0% w/v glycine, and 0.714 mg/ml for each of four HPV-16 E6 peptides (consisting of residues 1-45, 46-80, 81-115, and 116-158 of SEQ ID NO:1, each amidated at its carboxy terminus and acetylated at its amino terminus). The pharmaceutical solution A is withdrawn into a syringe in the amounts of 50 µg, 100 µg, 250 µg, or 500 µg (70 to 700 µl of solution A) and mixed in the syringe with 300 µl of CANDIN. The mixture in the syringe is then injected intradermally in an HPV-positive patient having cervical lesions.

CANDIN® (*candida albicans*) is made from the culture filtrate and cells of two strains of *Candida albicans*. The fungi are propagated in a chemically defined medium consisting of inorganic sals, biotin and sucrose. Lyophilized source material is extracted with a solution of 0.25% NaCl, 0.125% NaHCO$_3$ and 50% v/v glycerol. The concentrated extract is diluted with a solution of 0.5% NaCl, 0.25% NaHCO$_3$, 0.03% Albumin (Human) usp, 8 ppm polysorbate 80 and 0.4% phenol.

The potency of CANDIN® (*candida albicans*) is measured by DTH skin tests in humans. The procedure involves concurrent (side-by-side) testing of production lots with an Internal Reference (IR), using sensitive adults who have been previously screened and qualified to serve as test subjects. The induration response at 48 hours elicited by 0.1 mL of a production lot is measured and compared to the response elicited by 0.1 mL of the IR. The test is satisfactory if the potency of the production lot does not differ more than ±20% from the potency of the IR, when analyzed by the paired t-test (two-tailed) at a p value of 0.05

The potency of the IR is monitored by DTH skin testing. Persons included in the potency assay are qualified as test subjects by receiving four skin tests with the IR from which a mean induration response (mm) is calculated. Current skin tests with the IR must show that the potency of the IR has not changed more than ±20% from the mean qualifying response in the same test subjects, when analyzed by the paired t-test (two-tailed) at a p value of 0.05. The required induration response at 48 hours to the IR is 15 mm±20%.

The skin-test strength of CANDIN® (*candida albicans*) has been determined from dose-response studies in healthy adults. The product is intended to elicit an induration response ≥5 mm in immunologically competent persons with cellular hypersensitivity to the antigen.

Another embodiment provides a method of decreasing infection from human papilloma virus (HPV) in an individual or increasing regression of HPV-associated lesions in an HPV-positive individual, comprising: administering a pharmaceutical formulation comprising (a) one or more HPV E6 peptides, each of a length of 10-100 amino acid residues; (b) glutamate at a concentration of 2-40 mM; (c) trehalose at a concentration of 0.3% to 5% w/v; (d) glycine at a concentration of 0.2% to 10% w/v.

Another embodiment provides a method of decreasing infection from human papilloma virus (HPV) in an individual or increasing regression of HPV-associated lesions in an HPV-positive individual, comprising: administering the pharmaceutical composition to an HPV-positive individual in need thereof. In this case the pharmaceutical composition may be pharmaceutical composition comprising: an HPV E6 peptide A and one or more HPV peptides Y, the composition made by a method comprising: solubilizing an HPV E6 peptide A of 20 to 100 amino acids in length and comprising at least 20 consecutive residues of HPV E6 81-115 (residues 81-115 of SEQ ID NO:1) in a buffer that before the step of solubilizing the HPV peptide A contains in dissolved form two or more HPV peptides Y of 10 to 100 amino acids in length each that collectively comprise at least 50% of the sequence of HPV E6 1-80 (residues 1-80 of SEQ ID NO:1) and at least 50% of HPV E6 116-158 (residues 116-158 of SEQ ID NO:1) to create a final soluble composition containing the peptide A in dissolved form and the peptides Y in dissolved form.

In specific embodiments of these methods of treatment, the method comprises injecting the pharmaceutical composition intradermally. It may also be administered by other routes, including intravenous or subcutaneous injection, or enterally. But intradermal injection is the preferred route.

In specific embodiments of the methods of treatment, the pharmaceutical composition further comprises a recall antigen.

In specific embodiments of the method of treatment, the method further comprises injecting a recall antigen intradermally.

In specific embodiments, the method is a method of increasing regression of an HPV-associated lesion in an HPV-positive individual, and the lesion is a malignant tumor.

In specific embodiments, the lesion is a cervical carcinoma.

In specific embodiments, the lesion is a head and neck carcinoma.

In specific embodiments, the method is a method of increasing regression of an HPV-associated lesion, and the lesion is a cervical, vulvar, vaginal, penile, anal, or oropharyngeal tumor.

In a specific embodiment, the method is a method of increasing regression of an HPV-associated lesion, and the lesion is a high-grade squamous intraepithelial lesion (HSIL).

In other embodiments, the method is a method of increasing regression of an HPV-associated lesion in an HPV-positive individual, and the lesion is a benign tumor or a precancerous lesion.

The peptides in some embodiments are acetylated at their amino termini or amidated at their carboxy termini, or both. In other embodiments, neither terminus is modified.

Preferably in the method the composition is administered by intradermal injection. But it may be administered by any suitable method, for instance by intramuscular injection.

One embodiment provides a method of decreasing infection from human papilloma virus (HPV) in an individual or increasing regression of HPV-associated lesions in an HPV-positive individual, to induce a T cell response to HPV, the method comprising: administering to the individual a composition comprising one or more HPV antigens and administering to the individual a recall antigen that is not an HPV antigen; wherein the recall antigen is administered to be in contact with the one or more HPV antigens in the individual; wherein the individual is in need of a T cell response against the one or more HPV antigens. In specific embodiments, the one or more HPV antigens are E6 antigens or E7 antigens. In other specific embodiments, they are not E6 antigens. In another specific embodiment, they are not E7 antigens.

The method is expected to generate a stronger T cell response against the HPV antigens in the individual administering than an otherwise identical method that does not comprise administering a recall antigen that is not an HPV antigen. "Stronger T cell response" may be shown for example by greater antigen-specific T-cell mediated cytotoxicity or antigen-specific T cell proliferative response in vitro in T cells from a subject treated with a combination of a recall antigen and disease-specific antigen(s) versus from a subject treated with the disease-specific antigen(s) without the recall antigen. This can be demonstrated by testing of human subjects in a clinical trial or more likely in animal model testing, or by in vitro testing of T cells from a person, as for example shown in FIG. 3 of Example 2 below.

Preferably, the administration of the one or more HPV antigens and the recall antigen is performed by administering a composition comprising both the one or more HPV antigens and the recall antigen. But it can also be done by sequential separate administration of the one or more HPV antigens and the recall antigen, for instance by intradermal injection of the one or more HPV antigens in one composition and separate intradermal injection into the same spot of the recall antigen in a second composition.

Thus, in one embodiment, the composition comprising one or more HPV antigens also comprises the recall antigen.

In one embodiment, the steps of administering to the individual one or more HPV antigens and administering to the individual the recall antigen comprise intradermally injecting the one or more HPV antigens and the recall antigen. In other specific embodiments, the recall antigen and the HPV antigens are administered by subcutaneous injection. Intradermal injection is particularly preferred because Langerhans cells are the most common antigen presenting cells and are found in the greatest abundance in the skin.

In a specific embodiment, the one or more HPV antigens comprise an HPV E7 antigen.

In specific embodiments, the one or more HPV antigens are peptides of 8-100 amino acids in length, 8-70 amino acids in length, 8-50 amino acids in length, or 8-40 amino acids in length. In a more specific embodiment, the one or more peptides are chemically synthesized.

In a Phase I clinical trial of patients with women with biopsy-proven high-grade squamous intraepithelial (HSIL), women were treated with intradermal injection of a composition comprising HPV protein E6 residues 1-45 (SEQ ID NO:2), E6 46-80 (SEQ ID NO:3), E6 81-115 (SEQ ID NO:4), and E6 116-158 (SEQ ID NO:5), all mixed with CANDIN as an adjuvant. The dosages tested were 50 ug, 100 ug, and 250 ug of each of the peptides. It was surprisingly found that 4 of 6 subjects (67% in the 50 ug dose group, in 3 of 6 subjects (50%) in the 100 ug does group, and in 0 of 3 subjects in the 250 ug dose group had complete regression of their lesions. In addition, one additional subject in the 50 ug dose group had a partial regression (<0.2 mm2 lesion remaining) This is a surprising result that the lowest dose was the most effective. This is reported in Example 3 below.

Thus, another embodiment provides a unit dosage pharmaceutical composition comprising: 25 to 110 ug of a peptide consisting of SEQ ID NO:2, 25 to 110 ug of a peptide consisting of SEQ ID NO:3, 25 to 110 ug of a peptide consisting of SEQ ID NO:4, 25 to 110 ug of a peptide consisting of SEQ ID NO:5; and a recall antigen; in a unit dosage form for intradermal injection in a volume of 100 to 900 ul, 200 to 900 ul, 300 to 900 ul, or 100 to 600 ul.

The recall antigen should be in an amount and concentration sufficient to produce an induration response upon intradermal injection into a human—that is into a majority of immunocompetent adults who have previously been exposed to the antigen.

In a specific embodiment, the recall antigens is *Candida* extract.

In a specific embodiment, the unit dosage pharmaceutical composition comprises 200-400 ul of CANDIN or equivalent total potency of a *Candida* extract.

In a specific embodiment of the unit dosage pharmaceutical composition, the total volume is 200 to 500 ul.

In specific embodiments, the unit dosage pharmaceutical composition comprises 30 to 70 ug of each of the peptides, or in other embodiments about 50 ug of each of the peptides.

In specific embodiments, each of the peptides is acetylated at its amino terminus and amidated at its carboxy terminus.

In Example 3, the injecting the composition with 100 ug of each of the 4 peptides also worked well in causing regression of lesions. Thus, another embodiment provides a unit dosage pharmaceutical composition comprising: 55 to 150 ug of a peptide consisting of SEQ ID NO:2, 55 to 150 ug of a peptide consisting of SEQ ID NO:3, 55 to 150 ug of a peptide consisting of SEQ ID NO:4, 55 to 150 ug of a peptide consisting of SEQ ID NO:5; and a recall antigen; in a unit dosage form for intradermal injection in a volume of 100 to 900 ul.

Another embodiment provides a unit dosage pharmaceutical composition comprising: about 100 ug of a peptide consisting of SEQ ID NO:2, about 100 ug of a peptide consisting of SEQ ID NO:3, about 100 ug of a peptide consisting of SEQ ID NO:4, about 100 ug of a peptide consisting of SEQ ID NO:5; and a recall antigen; in a unit dosage form for intradermal injection in a volume of 100 to 900 ul.

Another embodiment provides a method of treating HPV infection comprising: administering to a patient intradermally a unit dosage pharmaceutical composition comprising: 25 to 110 ug of a peptide consisting of SEQ ID NO:2, 25 to 110 ug of a peptide consisting of SEQ ID NO:3, 25 to 110 ug of a peptide consisting of SEQ ID NO:4, 25 to 110 ug of a peptide consisting of SEQ ID NO:5; and a recall antigen; in a unit dosage form for intradermal injection in a volume of 100 to 900 ul.

In specific embodiments, the methods comprise injecting the patient intradermally with the unit dosage pharmaceutical composition on at least three successive occasions with no less than 5 days and no more than 28 days between each injection.

In another embodiment, the method comprises injecting the patient intradermally with the unit dosage pharmaceutical composition on at least three successive occasions with no less than 10 days and no more than 21 days between each injection.

In a specific embodiment, the method comprises injecting the patient intradermally with the unit dosage pharmaceutical composition on at least two successive occasions with no less than 10 days and no more than 21 days between each injection.

In a specific embodiment, the method comprises injecting the patient intradermally with the unit dosage pharmaceutical composition on at least three and no more than 6 occasions within a 2 year period with no less than 5 days and no more than 28 days between each injection.

It is shown herein in Example 2 that recall antigens, such as CANDIN, enhance the T cell immune response to the HPV peptides tested. A combination of a recall antigen and HPV peptides was contacted with peripheral blood mononuclear cells. Thus, administering a vaccine that includes a recall antigen together with disease-specific antigens may have general applicability to promote a cellular (T cell) immune response to the disease-specific antigens.

Thus, one embodiment provides a method of treating a disease caused by microorganism in a mammalian subject comprising: administering to the subject a composition comprising one or more antigens of the microorganism and administering to the subject a recall antigen that is not an antigen of the microorganism; wherein the recall antigen is administered to be in contact with the one or more antigens of the microorganism in the subject.

In specific embodiments, the microorganism may be a virus, bacteria, or fungus (for example, a yeast). In specific embodiments, the microorganism is not HPV. In specific embodiments, the microorganism is not herpes simplex virus.

The one or more antigens of the microorganism may be peptides in specific embodiments of 10-100, 8-100, 8-75, 8-50, 8-40, 10-75, 10-50, 10-40, 20-100, 20-75, 20-50, 20-40, 30-100, 30-75, 30-50, or 30-40 amino acid residues in length.

The peptides are preferably chemically synthesized, but they may also be produced in a recombinant organism from recombinant DNA technology. They may also be produced by other means known to persons of skill in the art, for instance by proteolysis of proteins of the microorganisms.

The peptides in some embodiments are acetylated at their amino termini or amidated at their carboxy termini, or both. In other embodiments, neither terminus is modified.

Preferably in the method the composition is administered by intradermal injection. But it may be administered by any suitable method, for instance by intramuscular injection.

EXAMPLES

Example 1. Solubilizing Amidated and Acetylated HPV E6 81-115 Peptide, and Formation of Pharmaceutical Formulation We attempted to make a pharmaceutical formulation with four HPV E6 peptides. The 4 peptides were peptides consisting of residues 1-45, 46-80, 81-115, and 116-158 of SEQ ID NO:1. Each of the peptides was amidated at its carboxyl terminus and acetylated at its amino terminus. The peptides were each chemically synthesized.

The HPV 16 E6 81-115 peptide was found to be insoluble in any suitable buffer for manufacturing. However, it was found that it could be solubilized and will stay soluble when added to 10 mM glutamate, pH 4.0 solution which already contains solubilized E6 1-45, E6 46-80, and E6 116-158 at 5 mg/ml concentration for each of the four peptides.

For the pharmaceutical formulation, this was mixed with trehalose as a stabilizing agent and glycine as tonicity modifier. The final concentrations of the formulation were 10 mM glutamate, 1.0% w/v trehalose, 2.0% w/v glycine, and 0.714 mg/ml each of the four peptides.

The formulation was lyophilized for storage, and reconstituted immediately before use by addition of the appropriate volume of water for injection to produce the concentrations stated above.

Example 2: *Candida* Skin Test Reagent as a Novel Adjuvant for a Human Papilloma Virus Peptide-Based Therapeutic Vaccine A vaccine adjuvant that can effectively promote cell-mediated immunity is currently not available. Because of the ability of a *Candida* skin test reagent injection to induce common wart regression, our group is using it as a novel adjuvant in a clinical trial of a peptide-based human papillomavirus therapeutic vaccine. The goal of this current study was to investigate the mechanisms of how *Candida* enhances the vaccine immune responses. Maturation effects on Langerhans cells, capacity to proliferate T-cells, expression of cytokines and pattern recognition receptors by Langerhans cells, and ability to induce Th1, Th2, and Th17 responses were investigated in healthy subjects. The vaccine, human papillomavirus peptides with *Candida*, demonstrated partial maturation effects on Langerhans cells indicated by significantly up-regulated CD40 ($p=0.00007$) and CD80 ($p<0.00001$) levels, and showed T-cell proliferative capacity ($p<0.00001$) when presented by Langerhans cells in vitro. Interestingly, the maturation effects were due to the peptides while *Candida* was responsible for the T-cell proliferation. The cytokine profile (IL-1β, IL-6, IL-8, IL-10, IL-12p40, IL-23Ap19, IFN-γ, and TNF-α) of Langerhans cells treated with the vaccine or *Candida* alone showed that IL-12p40 mRNA was most frequently induced, and IL-12p70 protein was detected in the supernatants. The presence of pattern recognition receptors known to associate with *Candida albicans* (DC-SIGN, dectin-1, dectin-2, galectin-3, mincle, mannose receptor, Toll-like receptors-1, 2, 4, 6, and 9) were demonstrated in all subjects. On the other hand, the induction of Th1 response demonstrated by IFN-γ secretion by CD4 cells stimulated with the vaccine or *Candida* pulsed Langerhans cells was demonstrated only in one subject. In summary, the Langerhans cell maturation effects of the vaccine were due to the peptides while the T-cell proliferative capacity was derived from *Candida*, and the most frequently induced cytokine was IL-12.

Abbreviations

APCs, antigen presenting cells; HPV, human papillomavirus; LCs, Langerhans cells; MFI, mean fluorescence intensity; PAMPs, pathogen-associated molecular patterns; PBMC, peripheral blood mononuclear cells; PE, phycoerythrin; qRT-PCR, quantitative real-time PCR; PRRs, pattern recognition receptors.

1. Introduction

The most widely used adjuvant in approved human vaccines is an alum-based adjuvant that has been shown to elicit a predominantly Th2 immune response [1]. Therefore, the alum-based adjuvant would be useful in a vaccine designed to boost antibody responses, but not for a vaccine designed to stimulate cellular immune responses. Since successful clearance of human papillomavirus (HPV) infection is believed to be induced by cell-mediated immunity [2, 3], an adjuvant that would promote such an immunity is necessary, but not available.

Our group and others have shown that serial intra-lesional injections of common warts with skin testing reagents such as *Candida*, mumps, and/or *Trichophyton* can induce regression not only of treated warts but also of distant untreated warts [4-9]. In a Phase I clinical trial (NCT00569231), our group used Candin® (Allermed, San Diego, Calif.), a colorless extract of *Candida albicans*, to treat common warts. Resolution of treated warts occurred in 82% of the subjects, and anti-HPV T-cell responses were demonstrated [8]. Given that Candin is derived from *C. albicans*, it should contain numerous pathogen-associated molecular patterns (PAMPs). We hypothesized that Candin would be an effective vaccine adjuvant which would stimulate multiple pattern recognition receptors (PRRs) and induce innate as well as adaptive immunity.

Cervical cancer is almost always caused by high-risk HPV infection, and is the $2^{nd}$ most common cancer among women in the world. Two very effective prophylactic HPV vaccines, Gardasil® (Merck, NJ, USA) and Cervarix® (GlaxoSmithKline, Middlesex, UK), are available, and they work by inducing high titers of neutralizing antibody [10-12]. However, they are not effective for women with pre-existing HPV infection [10, 12, 13]. Therefore, a therapeutic HPV vaccine that can be used for those already infected with HPV and/or have developed HPV-associated neoplasia is not available. Our group studied naturally induced immunity in women with HPV infection and/or cervical lesions, and have found that the ability to induce T-cell responses against E6, one of the oncoproteins of high-risk HPVs, is associated with HPV clearance and regression of cervical lesions [3, 14, 15]. Therefore, we designed an HPV therapeutic vaccine which consists of four HPV type 16 E6 peptides and Candin, and are conducting a Phase I clinical trial (NCT01653249).

In the current study, we examined the immune enhancing effects of Candin as a vaccine adjuvant. Surprisingly, the E6 peptides were responsible for the partial maturation of Langerhans cells (LCs) while Candin was responsible for the T-cell proliferative effects. The most commonly induced cytokine by the LCs was IL-12.

2. Materials and Methods 2.1 Generation of Monocytes-Derived LCs

Figure 1B:
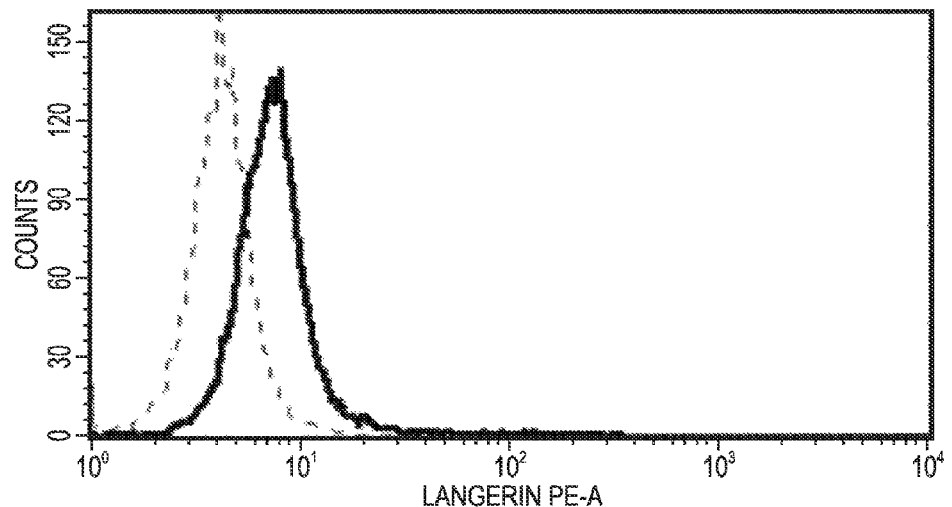
Figure 1C:
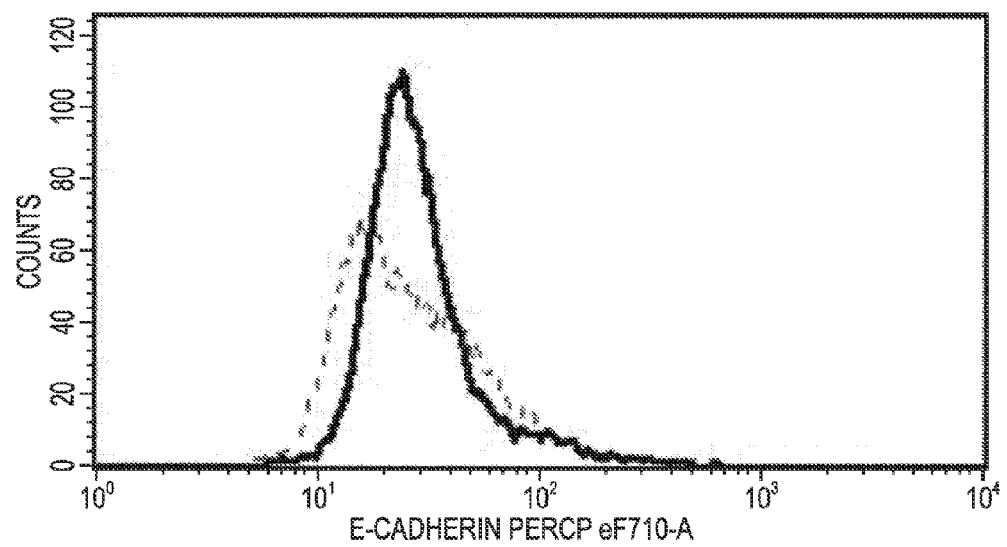

Mononuclear cells were collected from healthy blood donors (n=10) by apheresis (Key Biologics, LLC, Memphis, Tenn.). The subjects were numbered in a chronological order. Peripheral blood mononuclear cells (PBMCs) were purified using the ficoll gradient centrifugation method. Monocytes were negatively isolated from PBMC using Monocyte Isolation Kit II (Miltenyi Biotec, Auburn, Calif.), and were converted to LCs using granulocyte-macrophage colony-stimulating factor, IL-4, and transforming growth factor β-1 as described by Fahey et al. [17]. The effectiveness of conversion to LCs was demonstrated by detecting CD1a (eBioscience, San Diego, Calif.), Langerin (Beckman-Coulter, Brea, Calif.), and E-cadherin (eBioscience) using FACS Fortessa (University of Arkansas for Medical Sciences Microbiology and Immunology Flow Cytometry Core Laboratory) and CellQuest Pro software (BD Biosciences, San Jose, Calif.) in selected experiments (FIG. 1). Sufficient number of cells were available from all subjects except for subject 1 in whom the LC maturation experiment could not be performed.

2.2 Maturation Analysis of LCs Treated with Candin and/or HPV Peptides

Candin was dialyzed before use to remove a small amount of solvent (0.4% phenol) using Slide-A-Lyzer G2 Dialysis Cassette (Thermo Scientific, Rockford, Ill.). LCs were prepared as described above, and one million LCs each were treated with Candin (150 μl/ml), four current good manufacturing practice-grade HPV16 E6 peptides [E6 1-45, E6 46-80, E6 81-115, and E6 116-158 (referred to as "peptides" hereafter); 10 μg/ml/peptide; made by CPC Scientific, Sunnyvale, Calif. and vialed by Integrity Bio, Camarillo, Calif.], or Candin/"peptides". Zymosan (10 μg/ml, InvivoGen, San Diego, Calif.), a yeast cell wall particle containing many polysaccharides including β-glucan and mannan [18], was used as a positive control. After 48 hour incubation, cells were stained with anti-human CD40 phycoerythrin (PE)-Cy5.5, CD80 fluorescein isothiocyanate, CD86 PE-Cy5 and HLA-DR PE (eBioscience, San Diego, Calif.). Ten thousand events were acquired, and the data were analyzed using Flowjo software (BD Biosciences).

2.3 Analysis of T Cell Proliferation Induced by LCs Treated with Candin and/or "Peptides"

On day 7 of LCs conversion, CD3 T cells from the same subjects were negatively isolated from PBMCs using Pan T-Cell Isolation Kit II (Miltenyi Biotec). To remove CD25 regulatory T cells, human CD25 Antibody-Biotin (Miltenyi Biotec) was added. T cell proliferation assay was performed in 6 replicate wells by co-culturing T cells ($1.5 \times 10^6$ cells/ml) with autologous LCs ($3 \times 10^4$ cells/ml) in 100 µl of complete Yssel's media (Gemini Bioproducts Inc, Woodland, Calif.) containing 1% human serum in each well of a 96-well plate. Wells containing cells only (T-cells and LCs), cells and Candin (150 µl/ml), cells and Candin/"peptides", and cells and tetanus toxoid (500 ng/ml, EMD Milipore, Billerica, Mass.) were set up. After 7 days of incubation, 10 µl of alamarBlue (Life Technologies, Grand Island, N.Y.) was used to replace the corresponding volume of media in each well, then the plate was incubated at 37° C. for 6 hours. Fluorescence was measured (530 nm excitation wavelength and 590 nm emission wavelength) in media using BioTek Synergy-2 Multi Plate Reader (US BioTek, Seattle, Wash.).

2.4 Cytokine and PRR Analyses by Quantitative Real-Time PCR (qRT-PCR)

One million LCs each were treated with Candin (50 µl/ml, 100 µl/ml, and 150 µl/ml) with or without "peptides" (10 µg/ml/peptide) at each Candin concentration. Zymosan was used as a positive control at 10 ug/ml and media only as a negative control. Cells were harvested for RNA after 8 and 24 hours. RNA was extracted using RNeasy kit (Qiagen, Valencia, Calif.), and treated with DNase I (Promega, Madison, Wis.). cDNA synthesis was carried out using SuperScript III first-strand synthesis system (Life Technologies).

Quantitative PCR analysis was performed in duplicate for cytokines including IL-1β, IL-6, IL-8, IL-10, IL-12p40, IL-23Ap19, IFN-γ and TNF-α using an iQ-SYBR mix (Bio-Rad, Hercules, Calif.). In addition, expressions of PRRs (DC-SIGN, dectin-1, dectin-2, galectin-3, mincle, mannose receptor, TLR-1, TLR-2, TLR-4, TLR-6, and TLR-9) known to associate with C. albicans [19-28] were examined. The primers used to detect IL-12 were previously reported by Vernal et al. [29]. All other primers were designed using Beacon Design software (Bio-Rad, Table 1). The threshold cycles were normalized to a human housekeeping gene, glyceraldehyde 3-phosphate dehydrogenase, and were calculated as fold change over untreated LCs at 8 hours. mRNA was considered to be detected when amplification of cDNA was demonstrated.

2.5 IL-12p70 Protein Analysis by ELISA

Supernants from LCs treated with Candin (50 µl/ml, 100 µl/ml and 150 µl/ml) with or without "peptides" (10 µg/ml/peptide) from the qRT-PCR experiments at 24 hours were collected and tested using the IL-12p70 High Sensitivity ELISA kit (eBioscience). Values from media only wells were subtracted from experimental wells.

2.6 Intracellular Cytokine Staining

The methods were adapted according to those described by Zielinski et al. [30]. CD4 T-cells were negatively isolated from PBMCs using CD4 T Cell Isolation Kit II (Miltenyi Biotec) and were co-cultured with autologous LCs at a ratio of 50:1 (CD4 T-cells:LCs). Candin (150 µl/ml) with or without "peptides" (10 µg/ml/peptide) were added to stimulate cells. Media alone was used as a negative control. After 6 days of co-culture, the cells were stimulated with phorbol 12-myristate 13-acetate (200 nM, Sigma, St. Louis, Mo.), and ionomycin (1 µg/ml, Sigma) for 2 hours. Then, Brefeldin A (10 µg/ml, eBioscience) was added for additional 2 hours. After being stained using fixable viability dye eFluor 450® (eBioscience), the cells were permeabilized/fixed and stained with anti-human IFN-γ PE, IL-17A peridinin chlorophyll protein-Cy5.5, IL-4 allophycocyanin, or relevant isotype controls (eBioscience). Ten thousand events were acquired using FACS Fortessa. Live lymphocytes were gated, and the percentages of IFN-γ, IL-17A and IL-4 positive CD4 T-cells were analyzed using FACS Diva (BD Biosciences) and Flowjo softwares.

2.7 Statistical Analysis

Figure 2B:
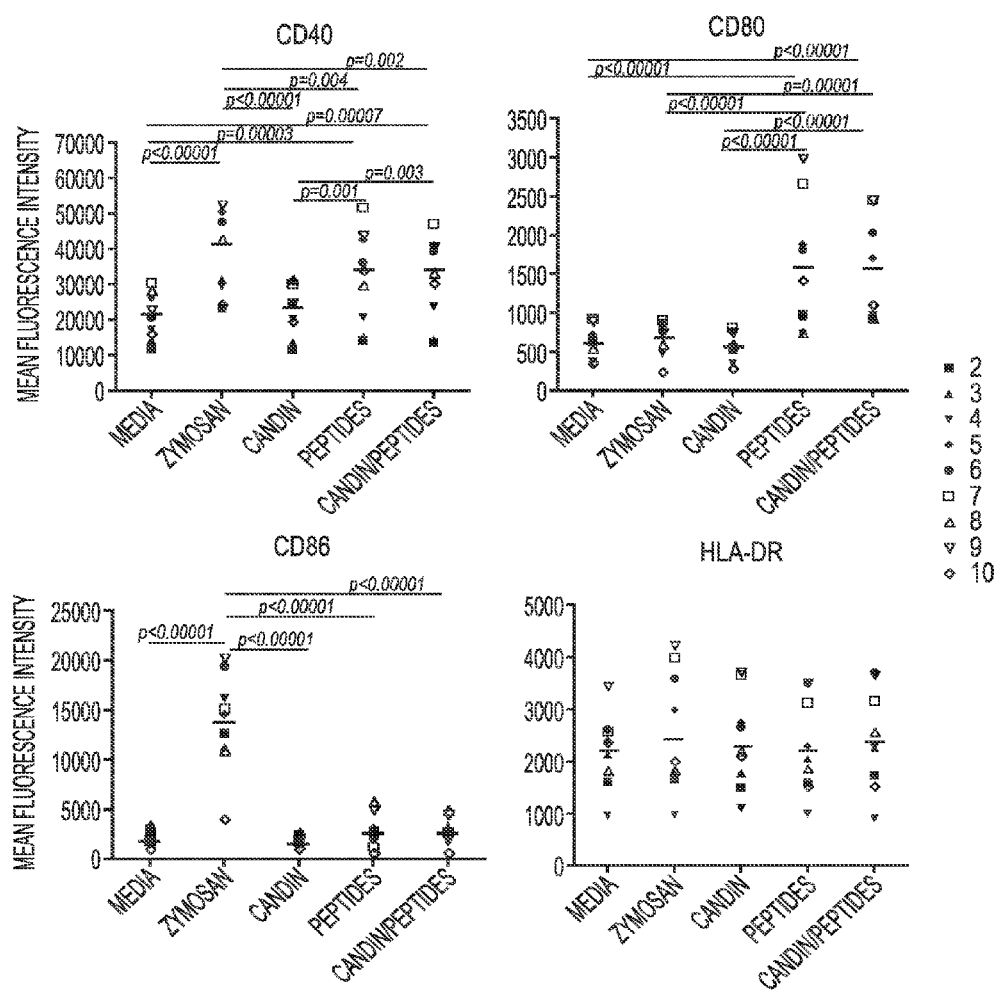
Figure 3:
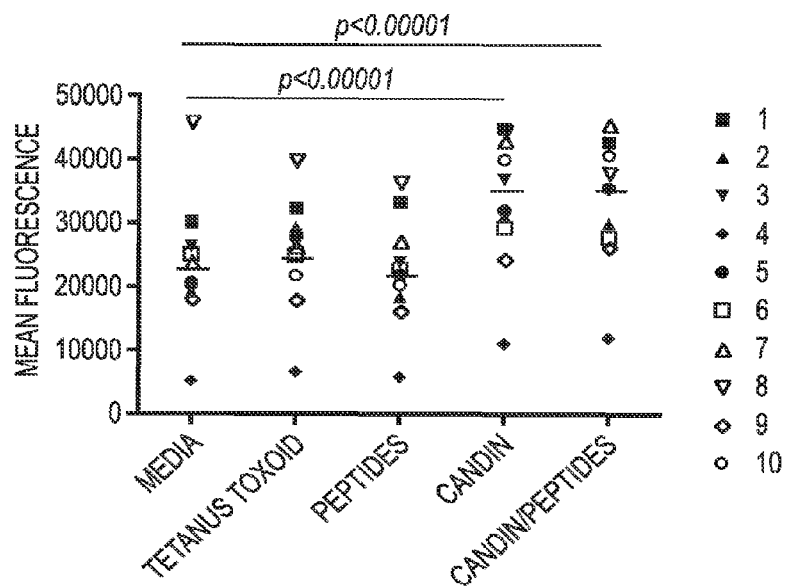
FIG. 3 T-cell proliferation measured using alamarBlue. Candin and Candin/"peptides" pulsed LCs induce significantly increased T-cell proliferation compared to media. All wells contained CD3 T-cells ($1.5 \times 10^5$ cells) and autologous LCs ($3 \times 10^3$ cells).

A mixed effects ANOVA was used to compare the groups while accounting for the dependence between groups. Tukey's multiple comparison procedure was used to perform all pairwise comparisons for maturation markers (FIG. 2B) while Dunnet's test was used to compare the media control values to the remaining groups for T-cell proliferation (FIG. 3).

3. Results 3.1 Phenotypic Maturation of LCs

Figure 2A:
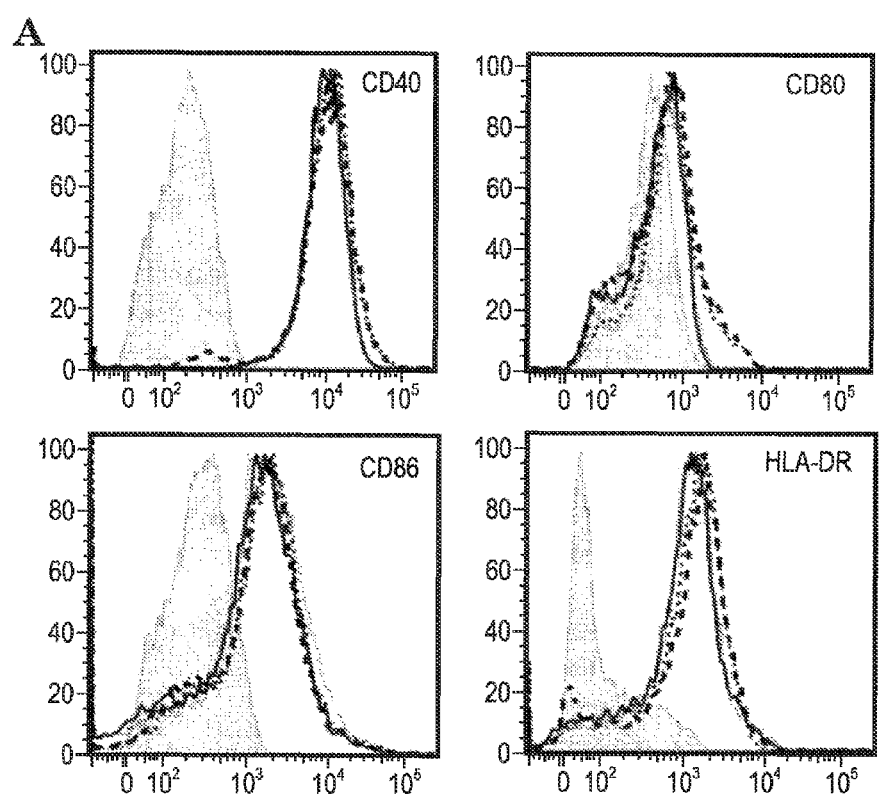
FIGS. 2A-B Maturation effects on LCs examined by surface expression of CD40, CD80, CD86, and HLA-DR. (A) Representative FACS histograms from subject 2. The shaded gray area, the black dotted line, the black solid line, the short dashed line and the long dashed line represent the isotype control, media, Candin, "peptides" and Candin/"peptides" respectively. (B) Summary of results from all subjects examined.

We evaluated the maturation effects of Candin, and/or "peptides" on LCs (FIGS. 1-2). For CD40, statistically significant increases in mean fluorescence intensity (MFI) were observed with LCs treated with zymosan ($p<0.00001$), "peptides" ($p=0.00003$) and Candin/"peptides" ($p=0.00007$) compared to untreated LCs. In addition, MFIs of LCs treated with "peptides" and Candin/"peptides" were significantly higher than the MFI of LCs treated with Candin alone ($p=0.001$ and $0.003$ respectively). For CD80, significant increases in MFIs were observed with LCs treated with "peptides" ($p<0.00001$) and Candin/"peptides" ($p<0.00001$) over media. Compared to Candin treated LCs, CD80 expression was significantly higher in "peptide" and Candin/"peptide" treated LCs ($p<0.00001$ for both). Only zymosan increased the MFI for CD86 significantly ($p<0.00001$). No significant increases were observed for HLA-DR. In summary, the "peptides" exerted partial LC maturation effects while Candin did not. Endotoxin levels for the "peptides" tested individually were all undetectable ($<1.0$ EU/mg).

3.2 T-Cell Proliferation Measured with alamarBlue

Proliferation was significantly increased with Candin ($p<0.00001$) and Candin/"peptides" ($p<0.00001$) over media (FIG. 3). "Peptides" did not induce measurable proliferation. Measurable proliferation with tetanus toxoid (increased fluorescence of ≥5000) was demonstrated in subjects 2 and 5, but overall no significant increase over media was observed (FIG. 3). Though unlikely, a possibility that LCs may have proliferated in addition to T-cells cannot be ruled out.

3.3 Expression of Cytokines by LCs Pulsed with Candin or Candin/"Peptides"

Figure 4:
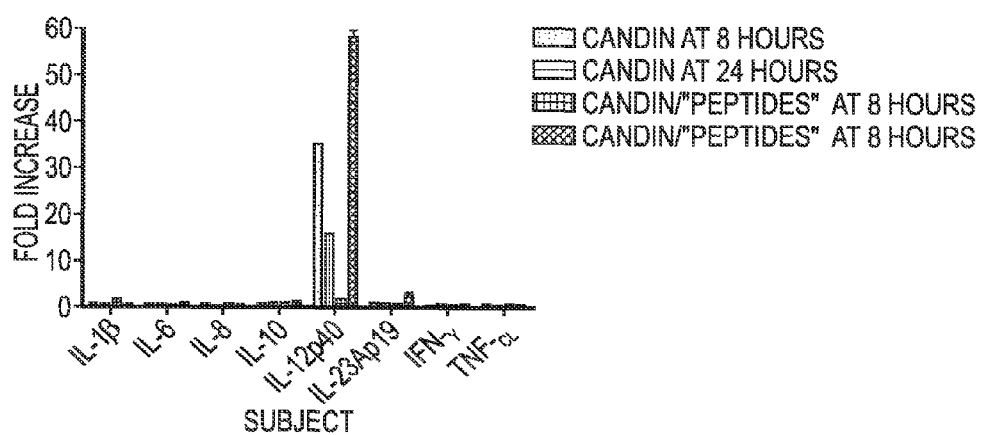
FIG. 4 Representative results of cytokine expression by LCs treated with Candin (150 µl/ml) or Candin/"peptides" from subject 4 are shown. The bars represent SD of the replicates.
Figure 5A:
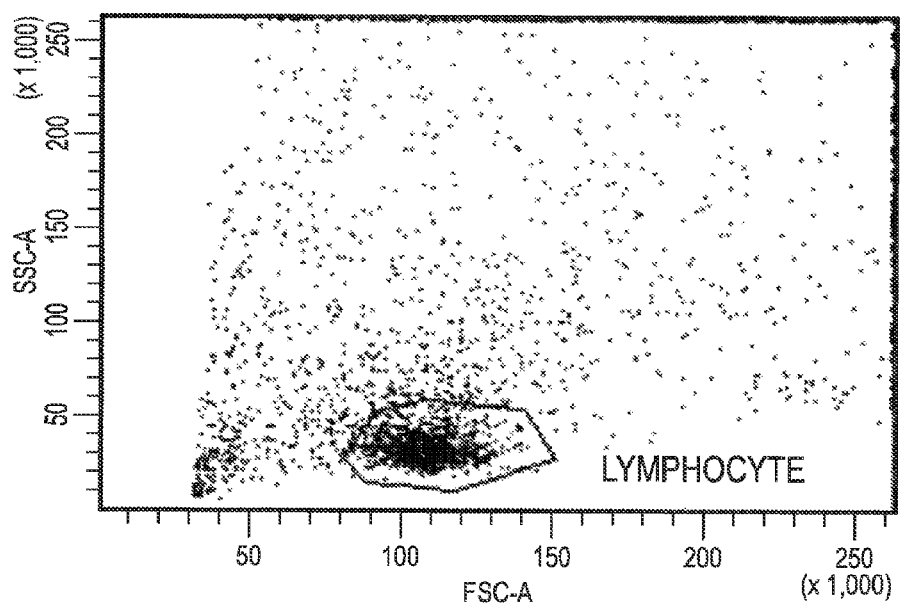
FIGS. 5A-I. Intracellular cytokine staining for IFN-γ, IL-4 and IL-17A of CD4 T-cells stimulated with LCs pulsed with Candin or Candin/"peptides". (A) A representative dot plot for subject 1 showing the gating on lymphocytes. (B) A representative dot plot for subject 1 showing gating on live cells discriminated using eFluor 450. (C) A representative dot plot for subject 1 showing IL-4 secreting CD4 cells that were exposed to LCs pulsed with Candin/"peptides". (D) Corresponding isotype control for IL-4. (E) A representative dot plot for subject 1 showing IFN-γ secreting CD4 cells that were exposed to LCs pulsed with Candin/"peptides". (F) Corresponding isotype control for IFN-γ. (G) A representative dot plot showing IL-17A secreting CD4 cells that were exposed to LCs pulsed with Candin/"peptides". (H) Corresponding isotype control for IL-17A. (I) Diagrams summarizing the results from all subjects.
Figure 5B:
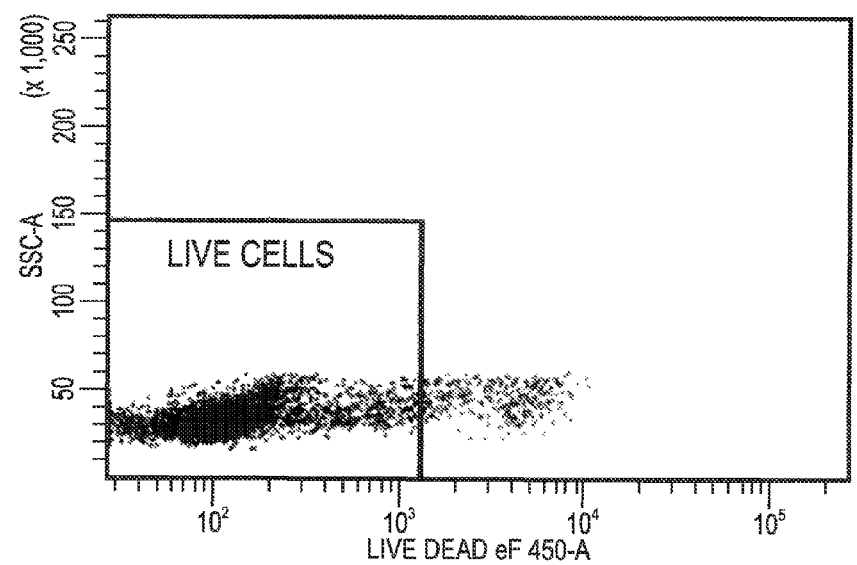
Figure 5C:
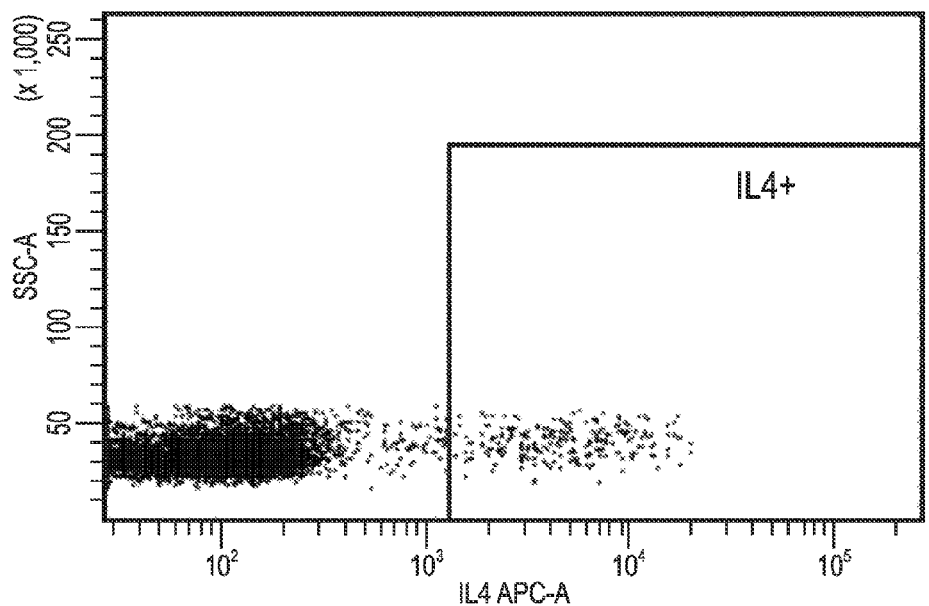
Figure 5D:
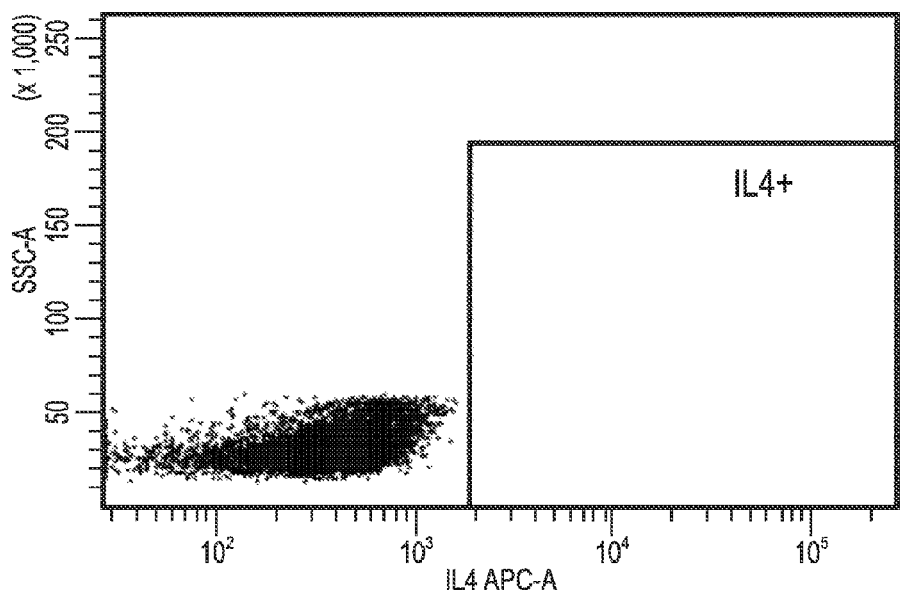
Figure 5E:
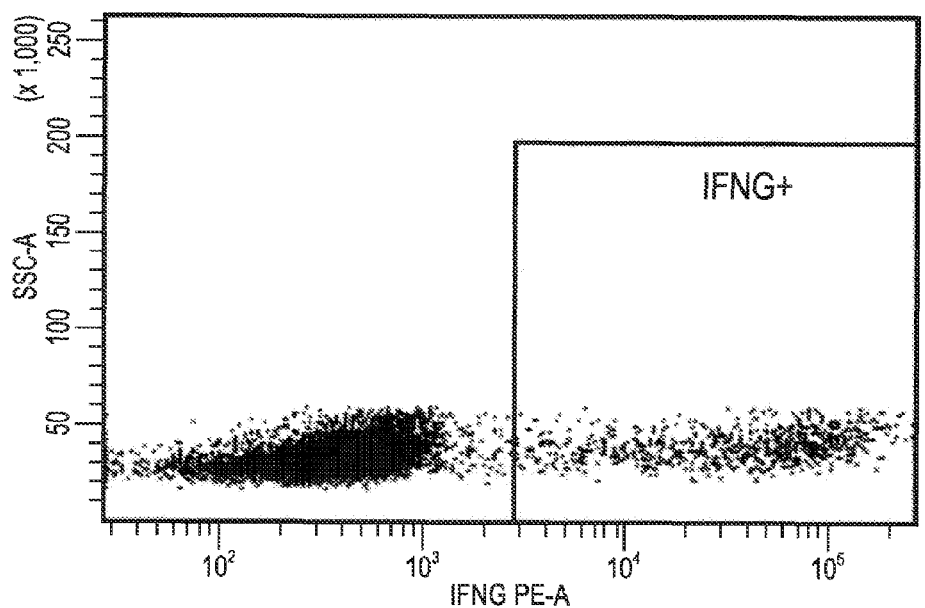
Figure 5F:
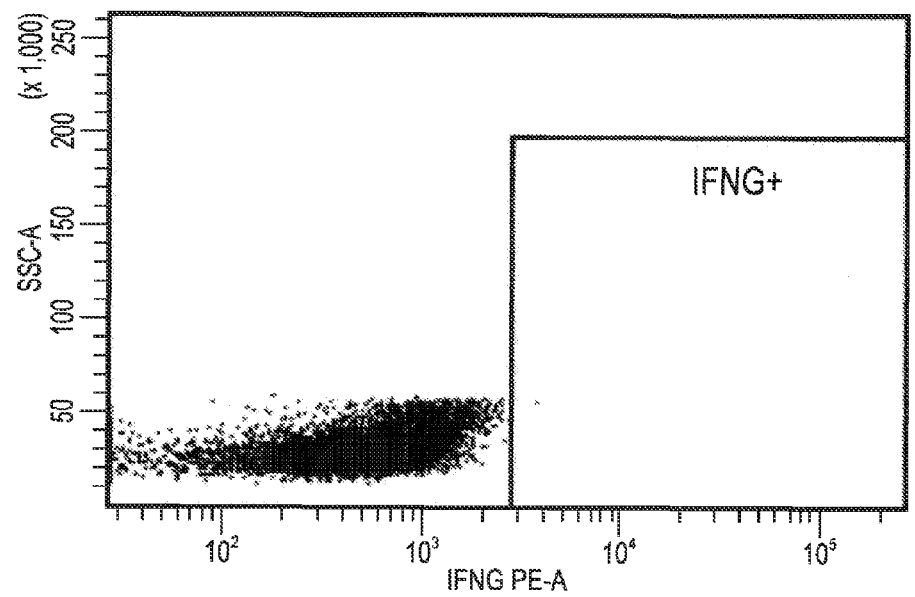
Figure 5G:
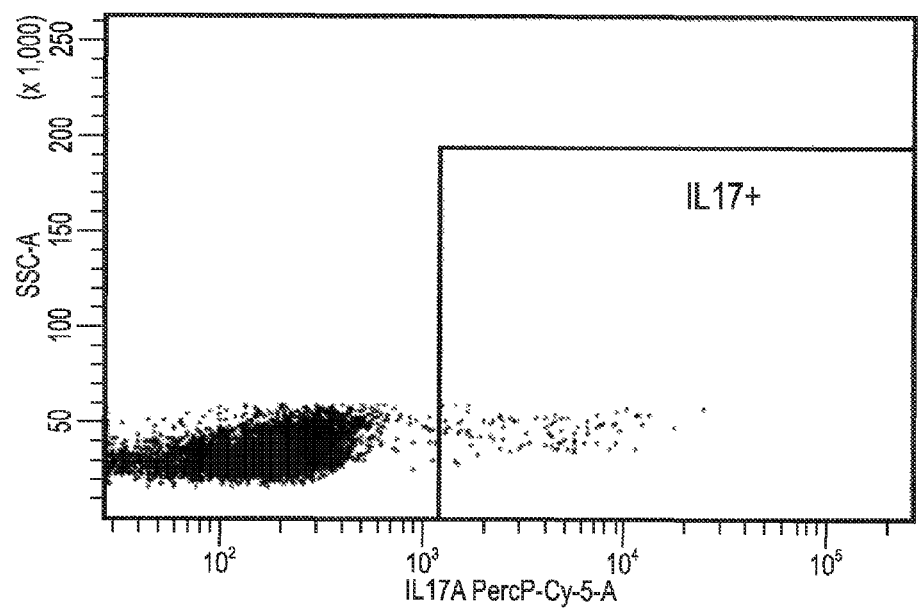
Figure 5H:
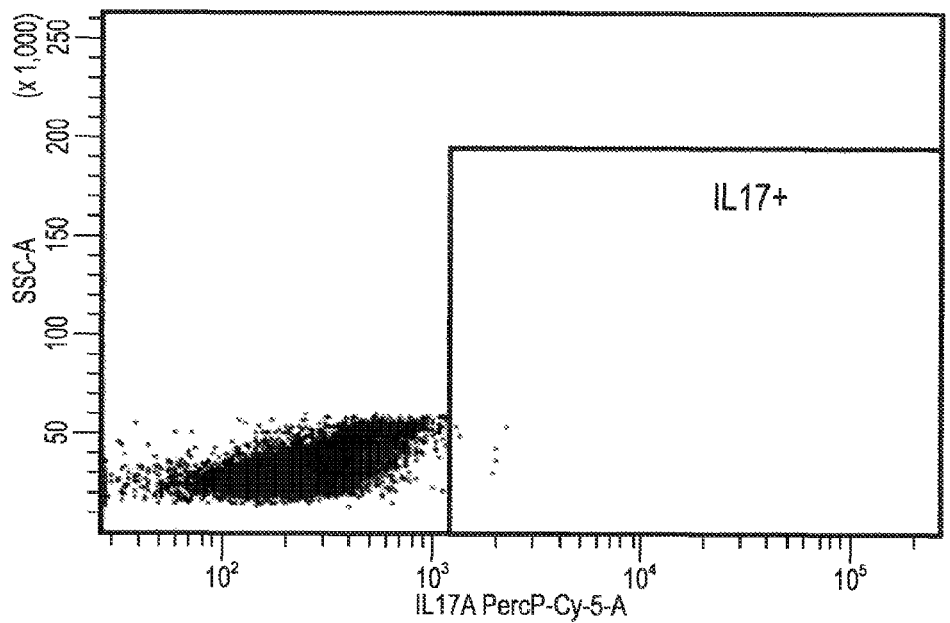
Figure 5I:
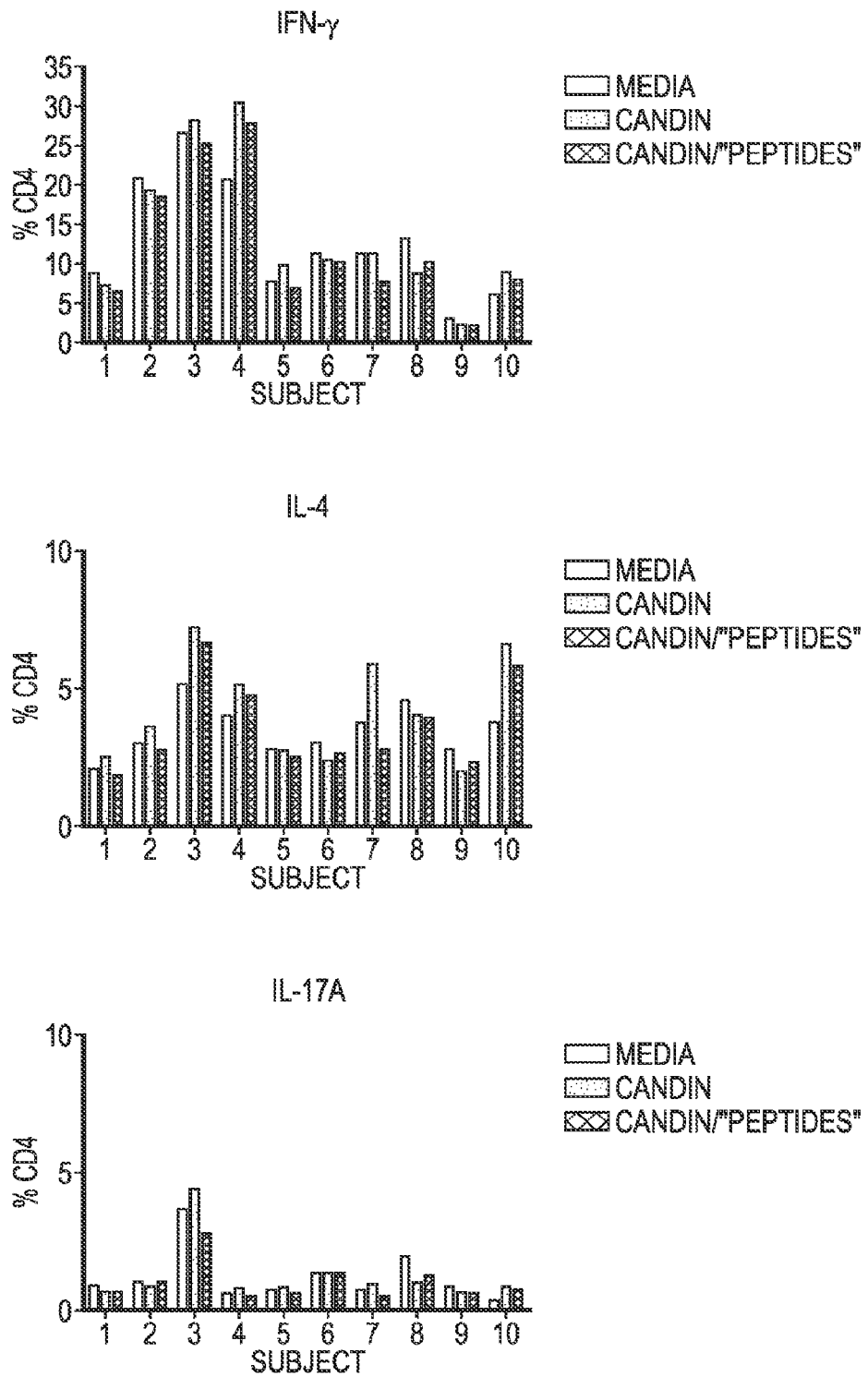

LCs from ten subjects were treated with Candin or Candin/"peptides", and mRNA expression of 8 cytokines (Table 1) were examined by qRT-PCR (FIG. 4, Table 2). The amplifications of the intended products were confirmed by DNA sequencing after gel-purification from selected experiments. Overall, the cytokine expression profiles of LCs treated with Candin and Candin/"peptide" were similar. IL-12p40 was the most commonly enhanced cytokine (≥5 fold over untreated), and expression was detected in 5 subjects with Candin and in 7 subjects with Candin/"peptides". IFN-γ was the $2^{nd}$ most commonly induced cytokine (6 subjects), and was detected in 5 subjects with Candin and in 4 subjects with Candin/"peptides". IL-1β was also induced in 6 subjects: 4 subjects with Candin and 6 subjects with Candin/"peptide". IL-6 and IL-23p19 were induced only with Candin (2 subjects for IL-6 and 1 subject for IL-23p19.) TNF-α was expressed only with Candin/"peptide" in 1 subject. IL-8 and IL-10 were not expressed in any subjects.

Supernatants from LCs treated with Candin or Candin/"peptides" for 24 hours were analyzed for the presence of IL12p70 protein. IL12p70 was detected in 27 of 30 samples treated with Candin (range 38 to 177 ng/ml) and in 27 of 30 samples treated with Candin/"peptides" (range 38 to 299 ng/ml).

TABLE 1

Primers used for qRT-PCR

| Description | Gene name | Accession no. | Forward primer sequence | Reverse primer sequence |
|---|---|---|---|---|
| Interleukin 1 beta | hIL-1β | NM_000576.2 | CAG GGA CAG GAT ATG GAG CAA C | CAC GCA GGA CAG GTA CAG ATT C |
| Interleukin 6 (interferon, beta 2) | hIL-6 | NM_000600.3 | GTA GTG AGG AAC AAG CCA GAG C | GGC ATT TGT GGT TGG GTC AGG |
| Interleukin 8 | hIL-8 | NM_000584.3 | GAC CAC ACT GCG CCA ACA C | AAA CTT CTC CAC AAC CCT CTG C |
| Interleukin 10 | hIL-10 | NM_000572.2 | GGG TTG CCA AGC CTT GTC TG | CGC CGT AGC CTC AGC CTG |
| Interleukin 12B | hIL-12p40 | NM_002187.2 | CCC TGA CAT TCT GCG TTC A | AGG TCT TGT CCG TGA AGA CTC TA |
| Interleukin 23 alpha subunit p19 (IL23A) | hIL23A p19 | NM_016584.2 | AGT GTG GAG ATG GCT GTG ACC | GGG CTA TCA GGG AGC AGA GAA G |
| interferon, gamma | hIFN-γ | NM_000619.2 | TGT GGA GAC CAT CAA GGA AGA C | TGC TTT GCG TTG GAC ATT CAA G |
| Tumor Necrosis Factor alpha | hTNF-α | NM_000594.3 | GGG GTG GAG CTG AGA GAT AAC C | ACG GCG ATG CGG CTG ATG |
| DC-SIGN, CD 209 | hDC SIGN | NM_001144899.1 | TGC AGT CTT CCA GAA GTA ACC GCT | TGT TGG GCT CTC CTC TGT TCC AAT |
| C-type lectin domain family 7, member A (CLEC7A) | hDectin1 | NM_197947.2 | TGC TTG GTA ATA CTG GTG ATA G | GGT TGA CTG TGG TTC TCT T |
| C-type lectin domain family 6, member A (CLEC6A) | hDectin2 | NM_001007033 | AAC ACA GAA GCA GAG CAG AAT | TCC AGA AGA CTA TTG AAG CAC ATT |
| Lectin, galactoside-binding, soluble, 3 (LGAL3) | hGalectin3 | NM_001177388.1 | TGT GCC TTA TAA CCT GCC TTT GCC | TTC TGT TTG CAT TGG GCT TCA CCG |
| C-type lectin domain family 4, member E (CLEC4E) | hMincle | NM_014358.2 | TCA GAA TAC CGG TGT GGC CTT TCT | TGG TTA CAG CCT GTT TGG AGC TGA |
| Mannose receptor, C type2 | hMRC2 | NM_006039.4 | AGC AAC GTC ACC AAA GAA ACG CAG | AGA ACT GTG CCT CTG ACC ACT TCA |
| Toll-Like Receptor 1/6* | hTLR1 or TLR6 | NM_003263.3 or NM_006068.4 | ATG TGG CAG CTT TAG CAG CCT TTC | TCT GGA AGA AAT CAG CCG ATG GGT |
| Toll-Like Receptor 2 | hTLR2 | NM_003264 | TGC TGC CAT TCT CAT TCT | CAC TCC AGG TAG GTC TTG |
| Toll-Like Receptor 4 | hTLR4 | NM_138557 | CGT GCT GGT ATC ATC TTC AT | GGT AAG TGT TCC TGC TGA G |
| Toll-Like Receptor 9 | hTLR9 | NM_017442.3 | ATC TGC ACT TCT TCC AAG GCC TGA | AAG GCC AGG TAA TTG TCA CGG AGA |
| Glyceraldehyde-3-phosphate dehydrogenase | hGAPDH | NM_002046.4 | GGA CCT GAC CTG CCG TCT AG | GTA GCC CAG GAT GCC CTT GA |

*The same primers were used to analyze TLR 1 and 6 amplifying a 100% homologous region between the two genes.

TABLE 2

A summary of qRT-PCR results for the three most commonly increased cytokines

| Cytokine | Candin ± peptides, time | 1 | 2 | 3 | 4 | 5 | 6 | 7 | 8 | 9 | 10 |
|---|---|---|---|---|---|---|---|---|---|---|---|
| IL-12p40 | 50 µl/ml, 8 h |  |  |  | 64 |  |  |  |  |  |  |
|  | 100 µl/ml, 8 h |  |  | 31 | 20 | 18 |  |  |  |  |  |
|  | 150 µl/ml, 8 h |  |  | 10 | 36 | 9 |  |  |  |  |  |
|  | 50 µl/ml + peptides, 8 h |  |  |  | 76 |  |  |  |  |  |  |
|  | 100 µl/ml + peptides, 8 h |  |  |  | 22 |  | 11 |  | 5 |  |  |
|  | 150 µl/ml + peptides, 8 h |  |  |  | 39 |  |  | 5 |  |  |  |
|  | 50 µl/ml, 24 h |  |  |  | 16 | 21 | 19 |  | 7 |  |  |
|  | 100 µl/ml, 24 h |  |  |  | 43 | 20 | 14 |  | 37 |  |  |
|  | 150 µl/ml, 24 h |  |  |  | 44 | 16 | 15 |  | 12 | 5 |  |
|  | 50 µl/ml + peptides, 24 h |  |  |  | 86 | 17 |  |  | 11 |  |  |
|  | 100 µl/ml + peptides, 24 h |  | 5 |  | 40 |  | 11 |  | 6 |  |  |
|  | 150 µl/ml + peptides, 24 h |  |  |  | 32 | 58 | 34 |  | 11 |  |  |
| IFN-γ | 50 µl/ml, 8 h |  |  |  |  |  |  |  | 29 |  |  |
|  | 100 µl/ml, 8 h |  |  |  |  |  | 9 | 13 | 64 |  |  |
|  | 150 µl/ml, 8 h |  |  |  |  |  | 12 | 44 |  |  |  |
|  | 50 µl/ml + peptides, 8 h |  |  |  |  |  | 15 |  | 5 |  |  |
|  | 100 µl/ml + peptides, 8 h |  |  |  |  |  | 11 | 18 | 37 |  |  |
|  | 150 µl/ml + peptides, 8 h |  |  |  |  |  |  | 42 | 25 |  |  |
|  | 50 µl/ml, 24 h |  | 29 |  |  |  |  |  | 5 |  |  |
|  | 100 µl/ml, 24 h |  | 92 |  |  |  | 13 | 17 | 49 |  |  |
|  | 150 µl/ml, 24 h |  |  |  |  |  |  | 10 | 23 |  |  |
|  | 50 µl/ml + peptides, 24 h |  |  |  |  |  |  | 13 |  |  | 19 |
|  | 100 µl/ml + peptides, 24 h |  |  |  |  |  |  | 12 | 23 |  |  |
|  | 150 µl/ml + peptides, 24 h |  |  |  |  |  |  | 17 |  |  |  |
| IL-1β | 50 µl/ml, 8 h |  |  |  |  |  |  |  |  |  |  |
|  | 100 µl/ml, 8 h |  |  |  |  |  |  | 5 | 20 |  |  |
|  | 150 µl/ml, 8 h |  |  |  |  |  |  | 5 |  |  |  |
|  | 50 µl/ml + peptides, 8 h |  |  |  |  |  | 23 | 8 |  | 14 | 7 |
|  | 100 µl/ml + peptides, 8 h |  |  |  |  | 7 | 19 | 8 | 7 | 7 |  |
|  | 150 µl/ml + peptides, 8 h |  |  |  |  |  | 10 | 10 | 8 |  |  |
|  | 50 µl/ml, 24 h |  |  |  |  |  |  |  |  | 91 |  |
|  | 100 µl/ml, 24 h |  |  |  |  |  | 5 |  |  | 5 |  |
|  | 150 µl/ml, 24 h |  |  |  |  |  |  |  |  |  |  |
|  | 50 µl/ml + peptides, 24 h |  |  |  |  |  | 8 |  |  |  |  |
|  | 100 µl/ml + peptides, 24 h |  |  |  |  |  | 7 |  | 7 |  |  |
|  | 150 µl/ml + peptides, 24 h |  |  |  |  |  | 6 |  |  |  |  |

Fold increases of ≥5 are shown.

3.4 Expression of PRRs on LCs

All 11 PRRs examined were detectable in untreated LCs of all subjects (data not shown). Upon stimulation with Candin or Candin/"peptides", few PRRs showed increased expression (≥5 fold over untreated). No obvious differences were observed in PRRs expressed between Candin and Candin/"peptide" treated LCs. The expression of TLR-9 was increased in 3 subjects (5 to 18 fold with Candin and 9 to 16 fold with Candin/"peptides"), mincle in 2 subjects (5 fold with Candin and Candin/"peptides"), mannose receptor in 2 subjects (5 to 9 fold with Candin and 5 to 11 fold with Candin/"peptides"), dectin-2 in 2 subjects (5 to 54 fold with Candin and 5 to 8 fold with Candin/"peptides"), and DC-SIGN in 1 subject (5 to 22 fold with Candin). In 5 subjects with increased expression of PRRs, 3 of them showed the increased expressions of two or more PRRs in LCs.

3.5 Intracellular Cytokine Expression of CD4 T-Cells Stimulated with Candin Pulsed LCs or Candin/"Peptides"-Pulsed LCs CD4 T-cells stimulated with Candin or Candin/"peptides"-treated LCs from ten subjects were stained for intracellular secretion of IFN-γ (Th1), IL-4 (Th2) and IL-17A (Th17) (FIG. 5). Increased IFN-γ secretions (>5%) were observed in CD4 T-cells exposed to Candin or Candin/"peptides"-treated LCs over media in subject 4 (9.5% and 6.9% respectively). Overall, no differences were seen in the secretion of IFN-γ, IL-4 and IL-17A between CD4 T-cells treated with LCs alone and LCs treated with Candin as well as between LCs alone and LCs treated with Candin/"peptides".

4. Discussion

"Adjuvant" is derived from a Latin word, adjuvare, and means to help or to enhance. An effective vaccine adjuvant should be able to promote a strong immune response against the vaccine antigen in terms of size and durability. Antigen presenting cells (APCs) play a critical role in the initiation of immune responses. One of the desired features of an adjuvant is the ability to enhance maturation of APCs and the consequent priming of effective T-cell responses. CD40 and CD80 have been demonstrated to be critical for the activation of antigen-specific T-helper cells [31] and cytotoxic T-cells [32]. Our results have shown that the "peptides" can induce significantly higher expression of CD40 and CD80. This HPV therapeutic vaccine may be a rare vaccine in that the peptide antigens rather than the adjuvant are more able to mature APCs. These results are different from those reported by Romagnoli et al. who showed up-regulation of CD40, CD80, CD86 and HLA-DR on dendritic cells by C. albicans [33]. Since endotoxin was undetectable in "peptides", it is unlikely that contamination may have contributed to the unexpected partial maturation effects on the LCs. We focused on examining maturation effects of LCs because our vaccine was formulated for intradermal route in order to take advantage of abundant LCs in epidermis. Studying maturation effects on other APCs such as dendritic cells and monocytes would be important in the future.

*C. albicans* as a component of the normal flora often colonizes the skin and the mucosal surfaces of healthy individuals. Underlying acquired immunity to *C. albicans* is usually present in immunocompetent individuals [34]. In this study, Candin and Candin/"peptides", but not "peptides", induced significant T-cell proliferation. Similar to our results, Gordon et al. demonstrated skin test positive reactions to *C. albicans* in 92% of healthy subjects [35], and Bauerle et al. demonstrated *Candida*-specific T-cell responses in 71% of healthy subjects. Candin is being used clinically to assess the intactness of cell-mediated immunity, so it is consistent with that that we find here that an extract from *C. albicans* has a T cell proliferative effect. Unfortunately, however, the maturation effects of *C. albicans* [33] are lost in the extract. On the other hand, it is found here that the "peptides" exert some maturation effects.

In creating this vaccine, an obstacle was encountered in being able to develop a formulation in which the "peptides" were soluble, as the E6 protein is known to be hydrophobic. While they remain soluble in acidic pH of the formulation, they are insoluble and form microparticles at a neutral pH (unpublished data). This unusual property may be contributing to the maturation effects by stimulating LCs to phagocytose these microparticles.

PRR signaling can induce APCs to express co-stimulatory molecules and cytokines necessary for activation and differentiation of T lymphocytes [37]. The cooperation of different PRRs in APCs by stimulating multiple PRRs leads to synergistic Th1 [20, 38] and cytotoxic T-lymphocyte responses [39]. *C. albicans* has been shown to activate many PRRs including DC-SIGN [19], dectin-1 [20], dectin-2 [21], galectin-3 [22], mannose receptor [19], mincle [40], and some TLRs [25-27, 41, 42]. Since some PRRs are increased during activation [43, 44], we investigated the presence and amplified expression of these PRRs. In this study, all PRRs examined were expressed by Candin and Candin/"peptide" pulsed LCs, and increased expressions of certain PRRs (DC-SIGN, dectin-2, mincle, monocyte receptor and TLR-9) were demonstrated in 5 of 10 subjects. Further investigations are necessary to determine which PRRs may have a role in transducing the signals from this HPV therapeutic vaccine. Dectin-1 in conjunction with TLR-2 can activate NF-κB [20], and dectin-1 can also independently mediate NFAT activation in dendritic cells leading to expression of inflammatory mediators such as IL-12p70 [45]. Therefore, it would be interesting to investigate whether Candin or Candin/"peptide" has any role in NF-κB and NFAT activation in the future.

Cytokines secreted by APCs play important roles in the process of differentiation of T-helper cells into Th1, Th2, or Th17 cells. IL-12p70 directs Th1 response while IL-1β and IL-6 direct the Th17 response [37, 46]. The cytokine profile in treated LCs showed IL-12p40 was the most commonly enhanced cytokine and IL-12p70 was also detected at a protein level. Published studies showed that *C. albicans* can induce the differentiation of specific Th1 and Th17 cells [30, 33], and *Candida*-specific Th1 immune responses can be detected in healthy subjects [47, 48]. These data lead us to anticipate the extract of *C. albicans*, Candin, to induce a Th1 and Th17 skewing effect. Though an increased Th1 response (IFN-γ secretion >5%) was observed in one subject, the overall results from ten subjects showed no skewing towards Th1 and Th17 responses. It may be that *Candida* exerts Th1 and Th17 effects through multiple mechanisms. There exist other subsets of APCs in dermis, like dermal DCs [49], which may play roles in the process of antigen presentation and T-cell activation. Furthermore, it would be important to assess the ability of this HPV therapeutic vaccine to induce HPV-specific T-cell responses. This is being investigated in the context of the ongoing clinical trial.

In summary, "peptides" (antigens) are responsible for the LC maturation effects while Candin (adjuvant) induces significant T-cell proliferation for this HPV therapeutic vaccine. Therefore, the antigens and the adjuvant have complementary immune enhancing effects. With time, the ongoing clinical trial will reveal whether these complementing effects will translate into effective clinical responses.

REFERENCES FOR EXAMPLE 2

[1] Gupta R K. Aluminum compounds as vaccine adjuvants. Adv Drug Deliv Rev. 1998; 32:155-72.

[2] Farhat S, Nakagawa M, Moscicki A B. Cell-mediated immune responses to human papillomavirus 16 E6 and E7 antigens as measured by interferon gamma enzyme-linked immunospot in women with cleared or persistent human papillomavirus infection. Int J Gynecol Cancer. 2009; 19:508-12.

[3] Nakagawa M, Gupta S K, Coleman H N, Sellers M A, Banken J A, Greenfield W W. A favorable clinical trend is associated with CD8 T-cell immune responses to the human papillomavirus type 16 e6 antigens in women being studied for abnormal pap smear results. J Low Genit Tract Dis. 2010; 14:124-9.

[4] Clifton M M, Johnson S M, Roberson P K, Kincannon J, Horn T D. Immunotherapy for recalcitrant warts in children using intralesional mumps or *Candida* antigens. Pediatr Dermatol. 2003; 20:268-71.

[5] Horn T D, Johnson S M, Helm R M, Roberson P K. Intralesional immunotherapy of warts with mumps, *Candida*, and *Trichophyton* skin test antigens: a single-blinded, randomized, and controlled trial. Arch Dermatol. 2005; 141:589-94.

[6] Johnson S M, Horn T D. Intralesional immunotherapy for warts using a combination of skin test antigens: a safe and effective therapy. J Drugs Dermatol. 2004; 3:263-5.

[7] Johnson S M, Roberson P K, Horn T D. Intralesional injection of mumps or *Candida* skin test antigens: a novel immunotherapy for warts. Arch Dermatol. 2001; 137:451-5.

[8] Kim K H, Horn T D, Pharis J, Kincannon J, Jones R, O'Bryan K, et al. Phase 1 clinical trial of intralesional injection of *Candida* antigen for the treatment of warts. Arch Dermatol. 2010; 146:1431-3.

[9] Phillips R C, Ruhl T S, Pfenninger J L, Garber M R. Treatment of warts with *Candida* antigen injection. Arch Dermatol. 2000; 136:1274-5.

[10] Quadrivalent vaccine against human papillomavirus to prevent high-grade cervical lesions. N Engl J Med. 2007; 356:1915-27.

[11] Harper D M. Currently approved prophylactic HPV vaccines. Expert Rev Vaccines. 2009; 8:1663-79.

[12] Schiller J T, Castellsague X, Villa L L, Hildesheim A. An update of prophylactic human papillomavirus L1 virus-like particle vaccine clinical trial results. Vaccine. 2008; 26 Suppl 10:K53-61.

[13] Hildesheim A, Herrero R, Wacholder S, Rodriguez A C, Solomon D, Bratti M C, et al. Effect of human papillomavirus 16/18 L1 viruslike particle vaccine among young women with preexisting infection: a randomized trial. JAMA. 2007; 298:743-53.

[14] Kim K H, Greenfield W W, Cannon M J, Coleman H N, Spencer H J, Nakagawa M. CD4+ T-cell response against human papillomavirus type 16 E6 protein is associated with a favorable clinical trend. Cancer Immunol Immunother. 2012; 61:63-70.

[15] Nakagawa M, Stites D P, Patel S, Farhat S, Scott M, Hills N K, et al. Persistence of human papillomavirus type 16 infection is associated with lack of cytotoxic T lymphocyte response to the E6 antigens. J Infect Dis. 2000; 182:595-8.

[16] Igyarto B Z, Kaplan D H. Antigen presentation by Langerhans cells. Curr Opin Immunol. 2013; 25:115-9.

[17] Fahey L M, Raff A B, Da Silva D M, Kast W M. Reversal of human papillomavirus-specific T cell immune suppression through TLR agonist treatment of Langerhans cells exposed to human papillomavirus type 16. J Immunol. 2009; 182:2919-28.

[18] Sato M, Sano H, Iwaki D, Kudo K, Konishi M, Takahashi H, et al. Direct binding of Toll-like receptor 2 to zymosan, and zymosan-induced NF-kappa B activation and TNF-alpha secretion are down-regulated by lung collectin surfactant protein A. J Immunol. 2003; 171:417-25.

[19] Cambi A, Netea M G, Mora-Montes H M, Gow N A, Hato S V, Lowman D W, et al. Dendritic cell interaction with *Candida albicans* critically depends on N-linked mannan. J Biol Chem. 2008; 283:20590-9.

[20] Gantner B N, Simmons R M, Canavera S J, Akira S, Underhill D M. Collaborative induction of inflammatory responses by dectin-1 and Toll-like receptor 2. J Exp Med. 2003; 197:1107-17.

[21] Sato K, Yang X L, Yudate T, Chung J S, Wu J, Luby-Phelps K, et al. Dectin-2 is a pattern recognition receptor for fungi that couples with the Fc receptor gamma chain to induce innate immune responses. J Biol Chem. 2006; 281:38854-66.

[22] Jouault T, El Abed-El Behi M, Martinez-Esparza M, Breuilh L, Trinel P A, Chamaillard M, et al. Specific recognition of *Candida albicans* by macrophages requires galectin-3 to discriminate *Saccharomyces cerevisiae* and needs association with TLR2 for signaling. J Immunol. 2006; 177:4679-87.

[23] Bugarcic A, Hitchens K, Beckhouse A G, Wells C A, Ashman R B, Blanchard H. Human and mouse macrophage-inducible C-type lectin (Mincle) bind *Candida albicans*. Glycobiology. 2008; 18:679-85.

[24] Netea M G, Gow N A, Munro C A, Bates S, Collins C, Ferwerda G, et al. Immune sensing of *Candida albicans* requires cooperative recognition of mannans and glucans by lectin and Toll-like receptors. J Clin Invest. 2006; 116:1642-50.

[25] Plantinga T S, Johnson M D, Scott W K, van de Vosse E, Velez Edwards D R, Smith P B, et al. Toll-like receptor 1 polymorphisms increase susceptibility to candidemia. J Infect Dis. 2012; 205:934-43.

[26] Villamon E, Gozalbo D, Roig P, O'Connor J E, Fradelizi D, Gil M L. Toll-like receptor-2 is essential in murine defenses against *Candida albicans* infections. Microbes Infect. 2004; 6:1-7.

[27] Netea M G, Van Der Graaf C A, Vonk A G, Verschueren I, Van Der Meer J W, Kullberg B J. The role of toll-like receptor (TLR) 2 and TLR4 in the host defense against disseminated candidiasis. J Infect Dis. 2002; 185:1483-9.

[28] Salvenmoser S, Seidler M J, Dalpke A, Muller F M. Effects of caspofungin, *Candida albicans* and *Aspergillus fumigatus* on toll-like receptor 9 of GM-CSF-stimulated PMNs. FEMS Immunol Med Microbiol. 2010; 60:74-7.

[29] Vernal R, Leon R, Silva A, van Winkelhoff A J, Garcia-Sanz J A, Sanz M. Differential cytokine expression by human dendritic cells in response to different *Porphyromonas gingivalis* capsular serotypes. J Clin Periodontol. 2009; 36:823-9.

[30] Zielinski C E, Mele F, Aschenbrenner D, Jarrossay D, Ronchi F, Gattorno M, et al. Pathogen-induced human TH17 cells produce IFN-gamma or IL-10 and are regulated by IL-1beta. Nature. 2012; 484:514-8.

[31] Schweitzer A N, Borriello F, Wong R C, Abbas A K, Sharpe A H. Role of costimulators in T cell differentiation: studies using antigen-presenting cells lacking expression of CD80 or CD86. J Immunol. 1997; 158:2713-22.

[32] Bennett S R, Carbone F R, Karamalis F, Flavell R A, Miller J F, Heath W R. Help for cytotoxic-T-cell responses is mediated by CD40 signalling. Nature. 1998; 393:478-80.

[33] Romagnoli G, Nisini R, Chiani P, Mariotti S, Teloni R, Cassone A, et al. The interaction of human dendritic cells with yeast and germ-tube forms of *Candida albicans* leads to efficient fungal processing, dendritic cell maturation, and acquisition of a Th1 response-promoting function. J Leukoc Biol. 2004; 75:117-26.

[34] Romani L Innate and adaptive immunity in *Candida albicans* infections and saprophytism. J Leukoc Biol. 2000; 68:175-9.

[35] Gordon E H, Krouse H A, Kinney J L, Stiehm E R, Klaustermeyer W B. Delayed cutaneous hypersensitivity in normals: choice of antigens and comparison to in vitro assays of cell-mediated immunity. J Allergy Clin Immunol. 1983; 72:487-94.

[36] Bauerle M, Schroppel K, Taylor B, Bergmann S, Schmitt-Haendle M, Harrer T. Analysis of the *Candida albicans*-specific T-cell response and oropharyngeal *Candida* colonization in a cohort of HIV-1-infected patients. Eur J Med Res. 2006; 11:479-84.

[37] Iwasaki A, Medzhitov R. Regulation of adaptive immunity by the innate immune system. Science. 2010; 327: 291-5.

[38] Napolitani G, Rinaldi A, Bertoni F, Sallusto F, Lanzavecchia A. Selected Toll-like receptor agonist combinations synergistically trigger a T helper type 1-polarizing program in dendritic cells. Nat Immunol. 2005; 6:769-76.

[39] Warger T, Osterloh P, Rechtsteiner G, Fassbender M, Heib V, Schmid B, et al. Synergistic activation of dendritic cells by combined Toll-like receptor ligation induces superior CTL responses in vivo. Blood. 2006; 108:544-50.

[40] Wells C A, Salvage-Jones J A, Li X, Hitchens K, Butcher S, Murray R Z, et al. The macrophage-inducible C-type lectin, mincle, is an essential component of the innate immune response to *Candida albicans*. J Immunol. 2008; 180:7404-13.

[41] Miyazato A, Nakamura K, Yamamoto N, Mora-Montes H M, Tanaka M, Abe Y, et al. Toll-like receptor 9-dependent activation of myeloid dendritic cells by Deoxynucleic acids from *Candida albicans*. Infect Immun. 2009; 77:3056-64.

[42] Netea M G, van de Veerdonk F, Verschueren I, van der Meer J W, Kullberg B J. Role of TLR1 and TLR6 in the host defense against disseminated candidiasis. FEMS Immunol Med Microbiol. 2008; 52:118-23.

[43] Biswas I, Garg I, Singh B, Khan G A. A key role of toll-like receptor 3 in tissue factor activation through extracellular signal regulated kinase 1/2 pathway in a murine hypoxia model. Blood Cells Mol Dis. 2012; 49:92-101.

[44] Sinha S, Guo Y, Thet S, Yuan D. IFN type I and type II independent enhancement of B cell TLR7 expression by natural killer cells. J Leukoc Biol. 2012; 92:713-22.
[45] Goodridge H S, Simmons R M, Underhill D M. Dectin-1 stimulation by *Candida albicans* yeast or zymosan triggers NFAT activation in macrophages and dendritic cells. J Immunol. 2007; 178:3107-15.
[46] Zhou L, Chong M M, Littman D R. Plasticity of CD4+ T cell lineage differentiation. Immunity. 2009; 30:646-55.
[47] La Sala A, Urbani F, Torosantucci A, Cassone A, Ausiello C M. Mannoproteins from *Candida albicans* elicit a Th-type-1 cytokine profile in human *Candida* specific long-term T cell cultures. J Biol Regul Homeost Agents. 1996; 10:8-12.
[48] Nisini R, Romagnoli G, Gomez M J, La Valle R, Torosantucci A, Mariotti S, et al. Antigenic properties and processing requirements of 65-kilodalton mannoprotein, a major antigen target of anti-*Candida* human T-cell response, as disclosed by specific human T-cell clones. Infect Immun. 2001; 69:3728-36.
[49] Valladeau J, Saeland S. Cutaneous dendritic cells. Semin Immunol. 2005; 17:273-83.

Example 3. Phase I Clinical Trial of a HPV Therapeutic Vaccine Containing E6 Peptides and CANDIN in Women with Biopsy-Proven High-Grade Squamous Intraepithelial Lesion A single-arm, open-label, dose-escalation Phase I clinical trial of a HPV therapeutic vaccine containing E6 peptides and CANDIN in women with biopsy-proven high-grade squamous intraepithelial (HSIL) is performed. The vaccine consists of a mixture of HPV peptides and CANDIN. The peptides are in a pharmaceutical solution A containing 10 mM glutamate, 1.0% w/v trehalose, 2.0% w/v glycine, and 0.714 mg/ml for each of four HPV-16 E6 peptides (consisting of residues 1-45, 46-80, 81-115, and 116-158 of SEQ ID NO:1, each amidated at its carboxy terminus and acetylated at its amino terminus). The pharmaceutical solution A is withdrawn into a syringe in the amounts of 50 ug, 100 ug, 250 ug, or 500 ug (70 to 700 ul of solution A) and mixed in the syringe with 300 ul of CANDIN. The mixture in the syringe is then injected intradermally in an HPV-positive patient having cervical lesions.

Figure 6:
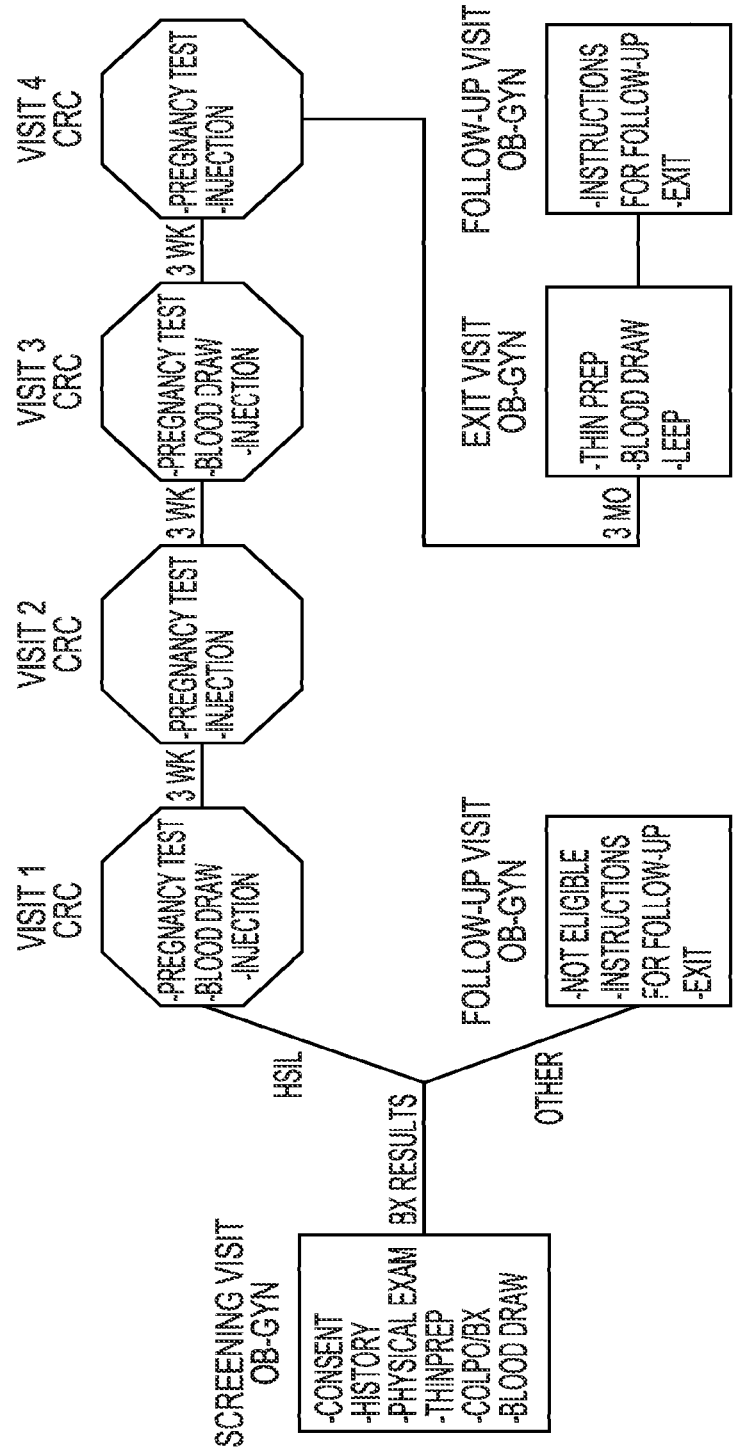
FIG. 6 shows diagram of a vaccination scheme. Each subject receives all the injections at the same dose. CRC, clinical Research Center; Colpo, colposcopy; Bx, biopsy.

Vaccine recipients are women with untreated biopsy-proven HSILs. Four injections (one every 3 weeks) of the vaccine are intradermally administered in upper extremities. Blood is drawn for CD3 ELISPOT (to assess CD4 and CD8 responses) and immune suppressor cell analysis before and after the second and fourth injections. Clinical response is assessed by performing LEEP excision after four injections. HPV-DNA testing is performed before and after four injections (FIG. 6). Each subject is given a single dose level for all four injections. The first cohort of six subjects receives a 50 ug dose; when the cohort is completed, the next subject receives the next higher dose level (detailed below and in FIG. 7). After all doses are tested (assuming no dose-limiting toxicity is observed), maximum tolerated dose (MTD), immunologically optimal dose (IOD), and clinically optimal dose (COD) are determined. An additional 30 subjects are vaccinated at the final dose (see below).

Figure 7:
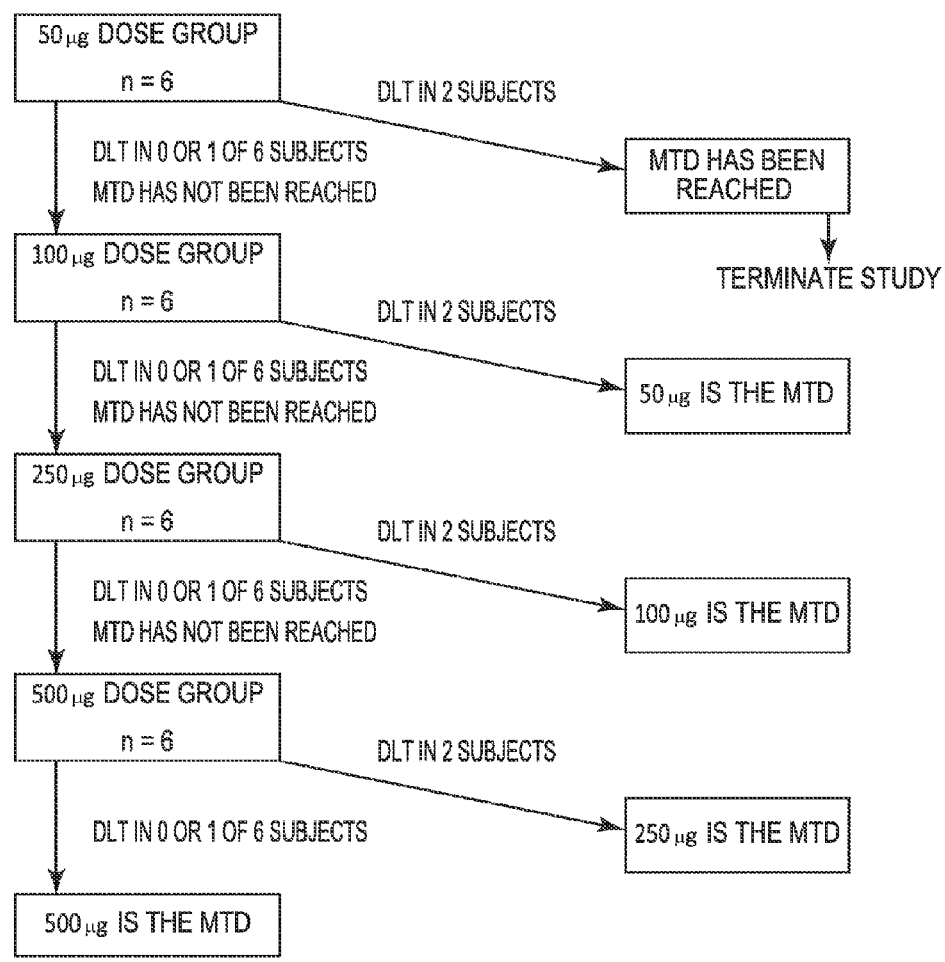
FIG. 7 shows dose-escalation plan of vaccination. A total of 24 subjects are enrolled in the dose-escalation phase, and an additional 30 subjects are recruited at the final dose.

The first six subjects each receive the lowest dose (50 ug) of each peptide as long as dose-limiting toxicity is not seen in more than one recipient. The first two subjects in each dose level are staggered by at least one week as per FDA recommendations. The dose level is increased as shown in FIG. 7 until maximum tolerated dose is reached or the study is completed. Thirty additional subjects are vaccinated at the final dose for further assessment of clinical response.

ThinPrep samples are tested for 37 HPV genotypes using the "Linear Array HPV Genotyping Test" according to the manufacturer's instructions (Roche Molecular Diagnostics, Inc., Alameda, Calif.). The HPV types to be tested include 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73, 81, 82, 83, 84, IS39, and CP6108. The human beta-globin signal is be assayed as a positive control for sample adequacy for DNA content from each sample. Positive-control samples (with added HPV plasmid DNA and plasmid-encoded human beta-globin gene) and negative-control samples (no HPV plasmid DNA and no human beta-globin gene) are provided by the manufacturer and are included in each experiment.

After each blood draw, PBMCs are separated into $CD14^+$ and $CD14^-$ populations and cryopreserved. To eliminate interassay variability, all three blood samples (before vaccination, after two vaccinations, and after four vaccinations) are used to establish T-cell lines and to perform ELISPOT assays. CD3 T-cell lines are established by stimulating in vitro magnetically selected CD3 cells with autologous mature dendritic cells exposed to HPV 16 E6-vac, E7-vac, E6-GST, and E7-GST. ELISPOT assays are performed as described (1). 16 regions within the HPV-16 E6 and E7 proteins (E6 1-25, E6 16-40, E6 31-55, E6 46-70, E6 61-85, E6 76-100, E6 91-115, E6 106-130, E6 121-145, E6 136-158, E7 1-25, E7 16-40, E7 31-55, E7 46-70, E7 61-85, and E7 76-98) are examined. The assay is performed in triplicate. In order to compare each region before vaccination and after 2 or 4 injections, a t test for paired samples is performed, as described previously (2). Therefore, each subject is assessed in terms of the number of regions with statistically significant increased T-cell responses after two injections or four injections.

To measure circulating Treg cells and Myeloid-derived suppressor cells (MDSC), a small amount of PBMCs ($2 \times 10^6$ cells) from each blood draw are used to monitor levels of circulating Tregs and MDSC to assess whether vaccination may inadvertently stimulate them (3). The number of $CD4^+$ $CD25^+$ forkhead box (FOX) $P3^+$ cytotoxic T lymphocyte-associated antigen-4 $(CTLA-4)^+$ cells are determined by flow cytometry using anti-human FoxP3 staining kit (allophycocyanin, eBiosciences, San Diego, Calif.), CTLA-4 peridinin-chlorophyll-protein complex (BD PharMingen, San Jose, Calif.), CD25 phycoerythrin, and CD4 fluorescein isothiocyanate (BD Biosciences, San Jose, Calif.) (4). Cells are analyzed by flow cytometry (XL-MCL, Beckman Coulter Inc., Fullerton, Calif.). The percent of circulating Treg cells (% $CD4^+CD25^+FoxP3^+CTLA-4^+$/total $CD4^+$) is determined before vaccination, after two, and after four injections. The Treg cells are considered to have increased if after two or four injections, the percent is at least two-fold greater than before injections. To enumerate MDSC, PBMCs are stained with CD14 and HLA-DR antibodies, and the percentage of $CD14^+HLA-DR^-$/low are assessed (5). Representative sections of LEEP specimens are used for immunohistochemical staining using FOXP3 (rabbit polyclonal; Abcam, Cambridge, Mass.) to innumerate the number of cervical Tregs (6). The densities of $FOXP3^+$ cells are determined using an image analysis software, and only cells with nuclear staining are counted.

Results:
Recruitment.

To date, 44 subjects have been enrolled, of which 27 had biopsy-proven HSILs and have received at least one vaccination (up to 27 additional subjects can be vaccinated before Apr. 12, 2015).

Safety.

Ninety-nine injections have been given to 27 subjects. No vaccine-related adverse events (AEs)>grade 2 have been reported (Table 3). (The two Grade 3 events in Table 3 were not vaccine related.) No grade 4 events at all have been reported.

occurred in 4 of 6 subjects (67% in the 50 ug dose group, in 3 of 6 subjects (50%) in the 100 ug does group, and in 0 of 3 subjects in the 250 ug dose group. A partial regression is defines as ≤0.2 mm$^2$ of HSIL lesion remaining at the end of study participation was observed in one subject in the 50 ug dose group and in another subject in the 250 ug does group.

The overall histological response rate was 60% (9 of 15), which is higher than the regression rates of historical placebo groups ranging from 22% to 28%. Two of 5 subjects (40%) with HPV 16 at baseline had regression, as did 7 of 10 subjects (70%) with HPVs other than type 16. None has progressed to squamous cell carcinoma.

TABLE 3

| | CTCAE Grade, Number of Events (Number of Patients) | | | | | | | | |
|---|---|---|---|---|---|---|---|---|---|
| | Grade 1 | | | Grade 2 | | | Grade 3 | | |
| | Dose (ug/peptide) | | | | | | | | |
| Adverse event | 50 | 100 | 250 | 50 | 100 | 250 | 50 | 100 | 250 |
| Injection site reaction, immediate$^a$ | 24 (6) | 24 (6) | 24 (6) | | | | | | |
| Injection site reaction, other, delayed$^b$ | 6 (3) | 23 (5) | 42 (6) | 1 (1) | 1 (1) | 9 (3) | | | |
| Myalgia | 9 (4) | 4 (1) | 4 (1) | | | | | | |
| Fatigue | 5 (3) | 1 (1) | 2 (1) | 1 (1) | | | | | |
| Diarrhea | 1 (1) | | | | | | | | |
| Nausea | 2 (2) | 5 (3) | | | | | | | |
| Headache | 3 (2) | 3 (3) | 5 (2) | | | | | | |
| Pain-body | 2 (2) | | | 1 (1) | | | | | |
| Alopecia | | | | 1 (1) | | | | | |
| Feverish$^c$ | 1 (1) | 2 (1) | 1 (1) | | | | | | |
| Muscle spasm | 1 (1) | | | | | | | | |
| Flu-like symptoms | 5 (2) | 3 (1) | 1 (1) | | 1 (1) | | | | |
| Anemia | | | | 1 (1) | | | | | |
| Vaginal infection | | | | 1 (1) | | 2 (1) | | | 1 (1) |
| Vulval infection | | | | | | 1 (1) | | 1 (1) | |
| Vaginal irritation | | | 1 (1) | | | | | | |
| Dizziness | | | 1 (1) | | | | | | |
| Agitation | | | 1 (1) | | | | | | |
| Epistaxis | | | 1 (1) | | | | | | |
| Neutropenia | 3 (3) | | | | | | | | |
| Hyokalmia | 4 (4) | 3 (3) | 3 (2) | | | 1 (1) | | | |
| Lymphocytosis | | | | 1 (1) | | | | | |
| AST increased | 1 (1) | 1 (1) | | | | | | | |
| ALT increased | 1 (1) | 1 (1) | | | | | | | |
| GGT increased | | 1 (1) | | | | | | | |

$^a$appearing <24 hours from time of vaccination;
$^b$appearing >24 hours from time of vaccination;
$^c$feeling warm without evidence of temperature >38.0 C.

The most common adverse events (AEs) were immediate and delayed injection-site reactions (a diffuse mild erythema at the site of injection).

In vitro investigation has unexpectedly revealed that the four cGMP peptides covering the HPV 16 E6 protein has maturation effects on Langerhans cells (LCs) as measured by up-regulated CD40 (p=0.00007) and CD80 (p<0.00001) levels [30]. These maturation effects are likely to be due to the formation of microparticles by peptides (which are soluble in acidic pH of the formulation) at a neutral pH. As insoluble microparticles are likely to be phagocytosed by LCs resulting in their activation and antigen presentation, the immediate and delayed injection site reactions observed during the Phase I clinical trial may be due to these microparticles.

Microparticles approximately 1-3 microns in diameter form when the peptides, solubilized in acidic pH, are mixed with neutral pH buffer. The microparticles form whether the peptides are mixed with *Candida* extract or not before adding to the neutral pH buffer.

Clinical Response.

The results from 15 vaccine recipients (mean age, 33.4±6.5 years old) are available. Complete HSIL regression Viral Clearance.

At least one HPV type became undetectable in 9 of 15 (60%) subjects. Seven of these 9 (78%) subjects showed clinical response.

Immunological Response.

Figure 8:
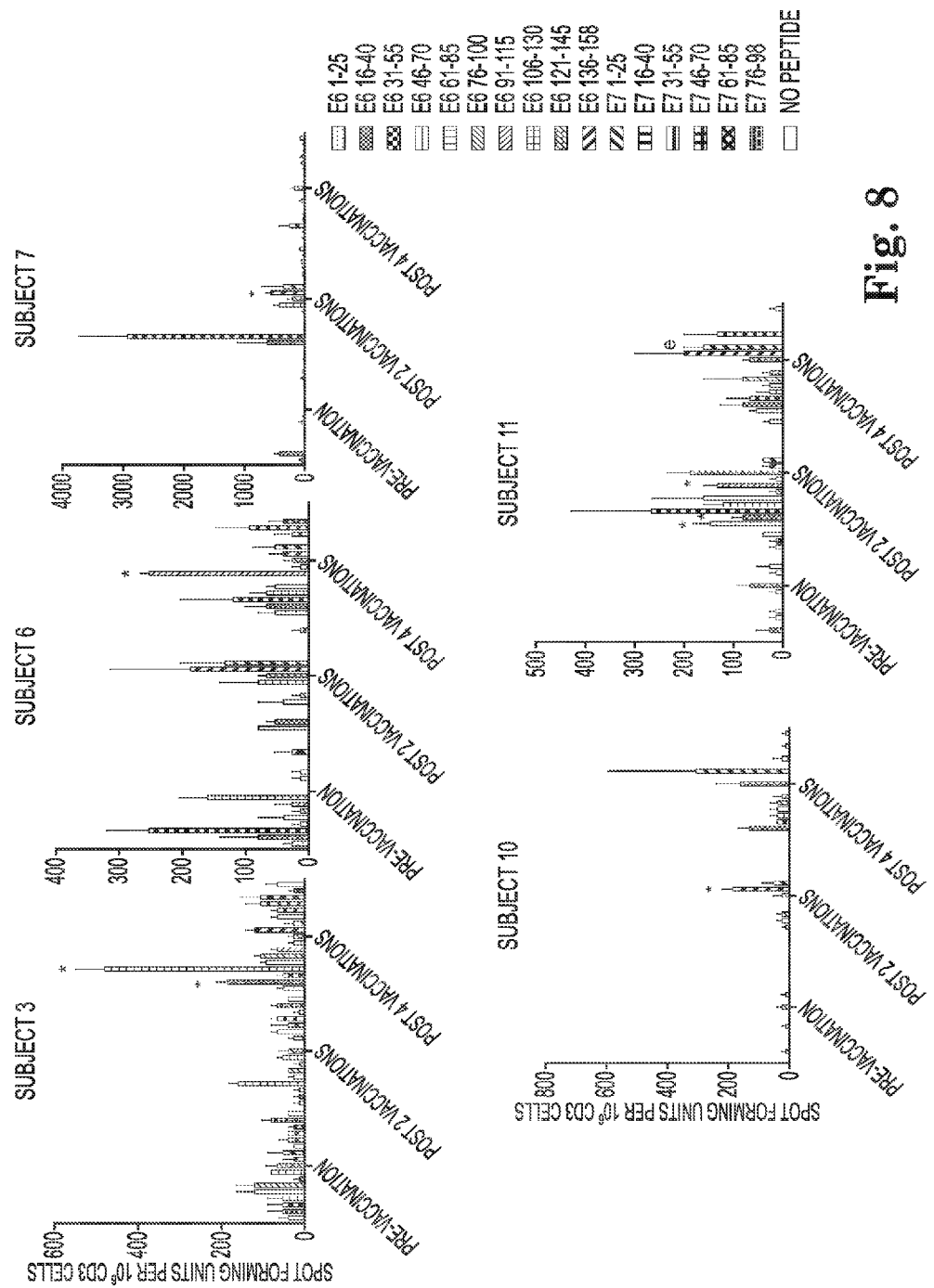
FIG. 8. HPV 16 E6 and E7 specific CD3 T-cell responses before vaccinations, after 2 vaccinations, and after 4 vaccinations. T-cell lines were established by stimulating CD3 T-cells with autologous dendritic cells pulsed with HPV 16 E6-vac, E6-GST, E7-vac, and E7-GST. Samples from different visits were tested in the same ELISPOT assay using overlapping peptides, and each region was tested in triplicate. Results of subjects who demonstrate statistically significant increases to the E6 peptides are shown, and the regions with significant increases determined using paired t-test are marked by "*". Subject 11, in whom HPV 16 was detected before and after vaccinations, also had a significant increase to E7 marked by "e" which may likely represent the first example of epitope spreading.

Vaccine-induced CD3 T-cell response to E6 were detected (positivity index ≥2) in 10 of 13 (77%) subjects and the increases were statistically significant in 6 subjects (46%). (FIG. 8).

Figure 9:
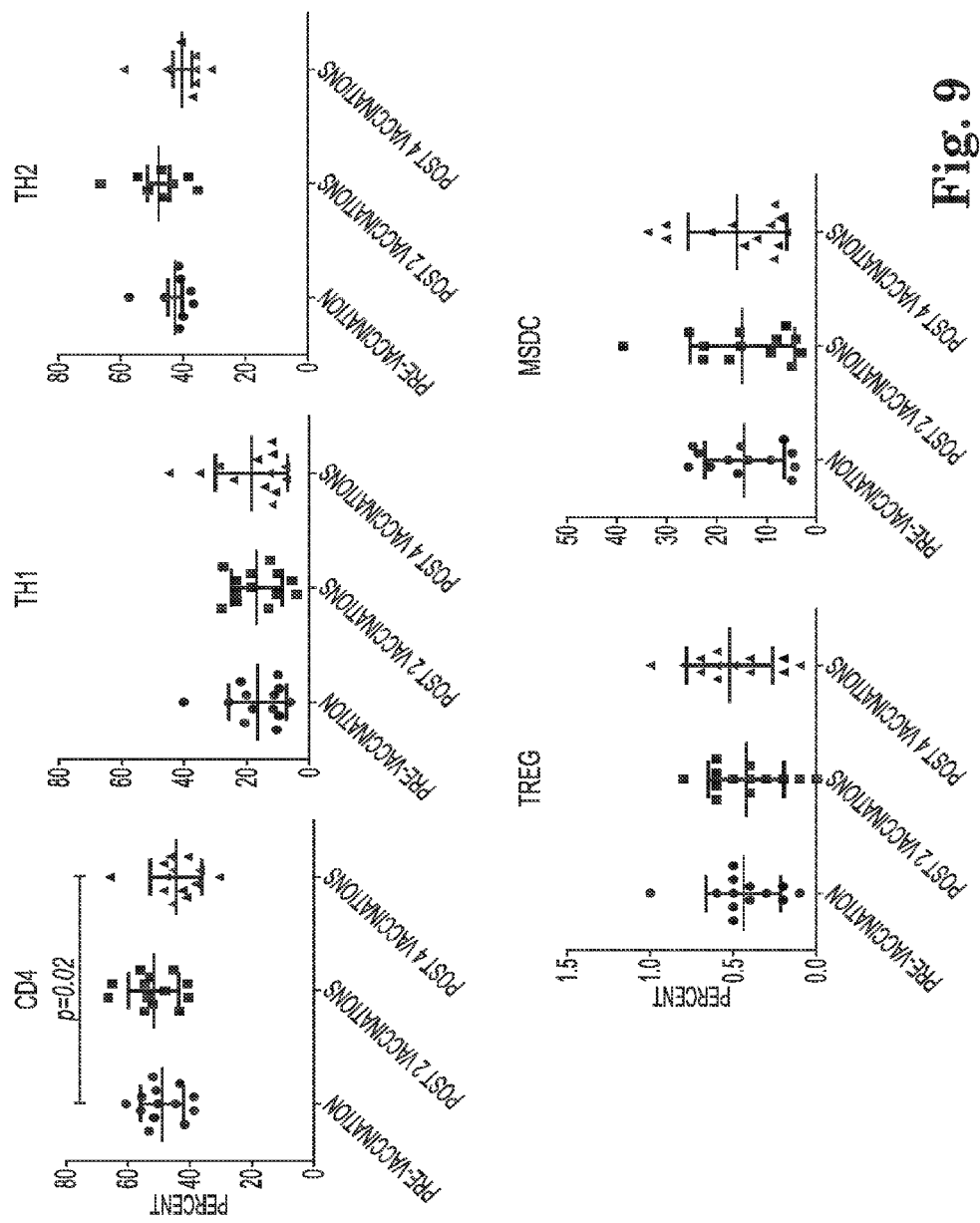
FIG. 9. Circulating immune cells before, after 2, and after 4 vaccinations in vaccine recipients (n=14). Percentages of lymphocytes are shown for CD4 cells. Percentages CD4 cells positive for CD4 and Tbet are shown for Th1 cells, positive for CD4 and GATA3 are shown for Th2 cells, and positive for CD4, CD25, and FoxP3 for Tregs. Percentages of monocytes positive for CD14 and HLA-DRlow/neg are shown for MDSC. The percentages of CD4 cells are significantly decreased after 4 vaccinations compared to before vaccination (paired t-test, p=0.02). The bars represent standard error of means.

The percentages of Th1 cells, Tregs, and myeloid-derived suppressor cells in periphery were unchanged while those of CD4 (p=0.02) and Th2 cells were decreased after vaccinations (FIG. 9).

No differences were measured in the numbers of FoxP3-positive Tregs in the lesions of non-responders (n=7) compared to those (CIN1 or representative normal region) of responders (n=7) in epithelium (127.4±174.9 per mm$^2$ versus 119.1±115.6 per mm$^2$) and in the underlying stroma (351.9±355 per mm$^2$ versus 380.4±152 per mm$^2$).

REFERENCES FOR EXAMPLE 3

1. Nakagawa M et al. Clin Diagn Lab Immunol. 2005; 12:1003-5.
2. Kim K H et al. Clin Vaccine Immunol. 2007; 14:362-8.
3. Banerjee D K et al. Blood. 2006; 108:2655-61.
4. Molling J W et al. International Journal of Cancer. 2007; 121:1749-55.
5. Hoechst B et al. Gastroenterology. 2008; 135:234-43.
6. Kobayashi A et al. Mucosal Immunology. 2008; 1:412-20.

Example 4. Phase II Clinical Trial

Need for HPV Therapeutic Vaccines

Although numerous preclinical and clinical trials have evaluated prophylactic HPV vaccines during the past few decades, these vaccines do not help those who already have established HPV infections [51]. Gardasil, a quadrivalent HPV L1 virus-like particle vaccine (HPV types 16, 18, 6, and 11), was the first to be FDA-approved in 2006; a bivalent version (HPV types 16 and 18), Cervarix, was approved by the FDA three years later. Clinical trials have demonstrated excellent vaccine efficacy in women negative for HPV 16 or HPV 18[52, 53], but the duration of protection remains to be determined, and a study of the bivalent vaccine showed no evidence of enhanced viral clearance in women with pre-existing HPV infections (n=1,259; 35.5% clearance in vaccinated group, 31.5% in a group receiving a negative control vaccine, p=NS) [51]. Therefore, therapeutic vaccines are needed for cases in which HPV infection is already established and in which HPV-related diseases have already developed. This is the particularly true because the prophylactic vaccine coverage rate in the targeted group (girls aged 13-17 years) has been reported to be only 32% nationally [54]. Although the standard surgical treatments for HSILs such as LEEP are very effective [14], their unintended side effect of increased incidence of preterm delivery from 4.4% to 8.9% [14, 15] has become a concern. Henceforth, the latest guideline no longer recommends treatment for CIN2 in young women (narrowly defined as ≤24 years old and broadly defined as any women who still plans to become pregnant [14]). Treatment is still recommended for CIN3 but observation is now considered acceptable. A new treatment which does not alter the anatomical integrity of the cervix like the HPV therapeutic vaccine is very much needed. In short, HPV therapeutic vaccines are needed because (1) prophylactic vaccines are not effective against established HPV infection, (2) utilization of the prophylactic vaccines has been low, (3) therapeutic vaccines would leave the cervix intact and would likely not increase the risk of preterm deliveries, and (4) therapeutic vaccine maybe effective against other cancers caused by HPV such as anal, oropharyngeal, penile, vaginal, and vulvar cancers.

1.5.2 Rationale for Proposed Dose of HPV Peptides

In the Phase I clinical trial, four dose levels (50, 100, 250, and 500 ug per peptide) were tested. The dose level with the highest clinical response will be selected to be used in the Phase II clinical trial. Thus far, the 50 ug per peptide dose has a higher response rate (67% complete response and 17% partial response) compared to the 100 ug per peptide (50% complete response).

The initial four dose levels were chosen based on information available in the literature. Published studies of clinical trials using various peptide vaccines reported using doses that range from 5-3,000 ug per peptide [31-38]. Optimal doses (and smaller doses if two dose levels were the same) for achieving immunogenicity differed greatly among the vaccines: 30 ug of 96-mer malaria peptide [31], 500 ug of 9-mer peptide for treating prostate cancer [34], 50 ug each of 13 HPV 16 E6 and E7 peptides ranging from 25 to 35 amino acids long [35]. Therefore, the dose levels likely to elicit the optimal immunogenicity were chosen.

The clinically optimal dose from the four doses (50, 100, 250, and 500 ug/peptide/injection) examined in the Phase I study as determined by the highest rate of histological regression will be used as the dose for the Phase II clinical trial.

1.5.3 Rationale for Proposed Dose of Candin®

Three hundred (300) µl of Candin® will be administered per injection, which was the amount used for intralesional injection of warts [47, 55], as well as the amount of Candin as a vaccine adjuvant in the Phase I clinical trial. The same amount will be used for the Phase II clinical trial as this amount has been shown to be safe and effective.

1.5.4 Rationale for Proposed Route of Injections

Intradermal route of administration will be used to make use of LCs as antigen-presenting cells. This route has also been shown to be safe, effective, and immunogenic in the Phase I clinical trial, and will be used for the Phase II clinical trial.

1.5.5 Rationale for Proposed Site of Injections

Extremities have been chosen as the site of administration because of the ease of access as well as availability of sufficient data demonstrating efficacy of HPV peptides delivered at these sites [35, 56]. As injecting in limbs has shown to be safe, effective, and immunogenic in the Phase I clinical trial, the same sites will be used for injection in the Phase II clinical trial.

1.5.7 Rationale for Interval Between Injections

The interval between injections ranged from 2 weeks to 90 days in the published studies [31-38], but most used a 3-week interval. Kenter and colleagues reported that peptide vaccine immunogenicity measured by IFN-γ ELISPOT assay was less prevalent when blood samples were drawn 7 days after the last vaccination but was higher when they were drawn 3 weeks after the last vaccination [35]. Therefore, we chose the 3-week (±7 days) interval because it appears to be long enough to allow sufficient mounting of immune responses. As this interval has been shown to be safe, effective, and immunogenic, the same interval will be used in the Phase II clinical trial.

Figure 10:
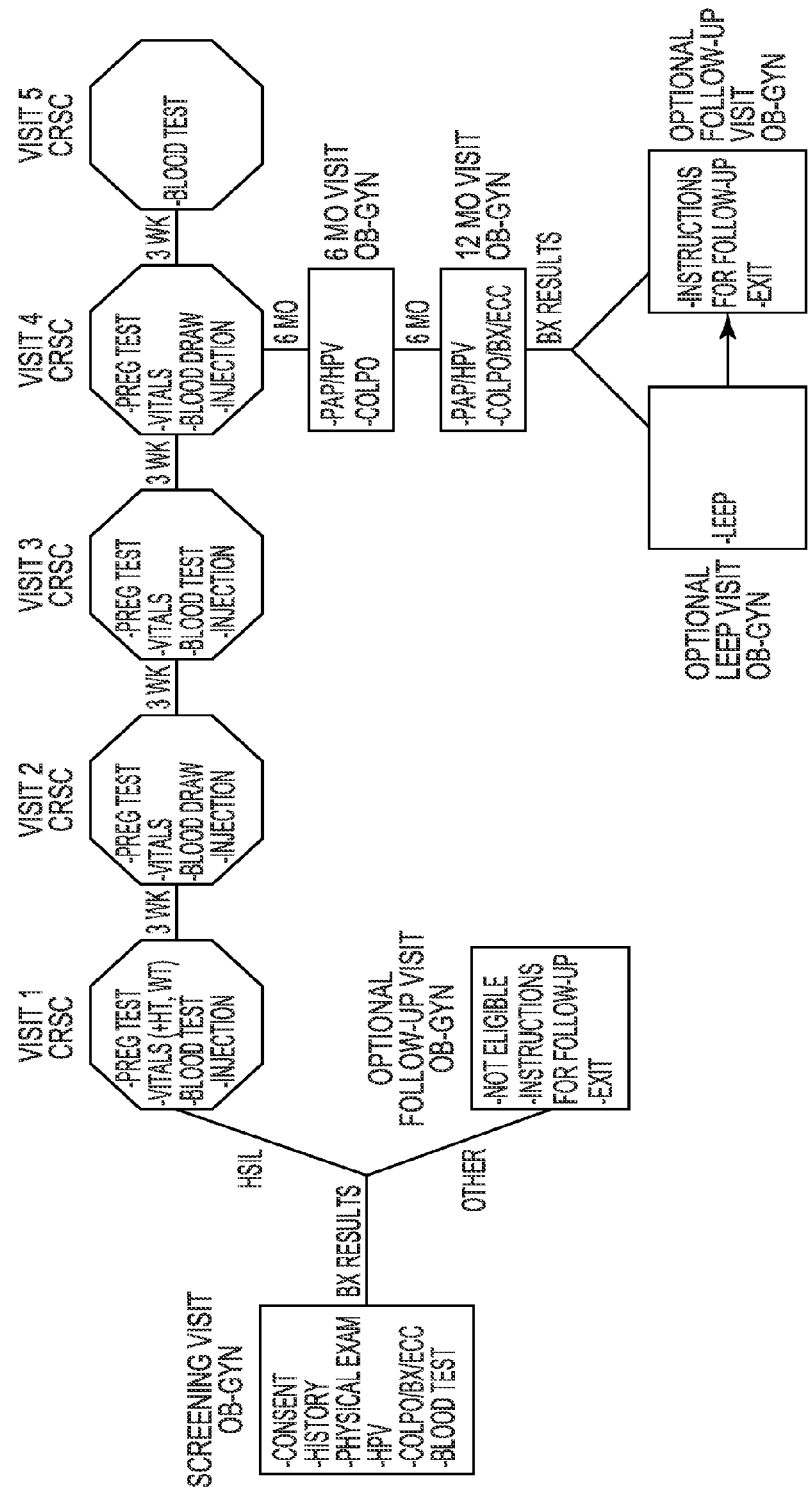
FIG. 10. Schematic presentation of study visits scheduled for the Phase II clinical trial of our HPV therapeutic vaccine. Blood tests are for clinical analyses. Blood draws are for scientific analyses. CRSC, Clinical Research Services Core Unit; Colpo, colposcopy, Bx, biopsy, ECC, endocervical curettage, LEEP, loop electrosurgical excision procedure.

1.5.8 Rationale for Interval Between the Last Injection and Final Histologic Assessment While histological response was assessed 3 months after the last vaccination by performing LEEP in the Phase I clinical trial, the full effect is known to take 1 year [17-19]. In the Phase II clinical trial, PepCan will be administered as an alternative to LEEP, and histological response will be assessed by obtaining colposcopy-guided biopsy 12 months after the last injection (FIG. 10). In a clinical trial which used a similar peptide-based HPV therapeutic vaccine to treat high-grade vulvar intraepithelial lesions, histological regression increased from 25% to 47% between 3 months and 12 months post-vaccinations [18].

1.5.9 Rationale for Primary Outcome Measure: Efficacy

The clinical response to evaluate the vaccine efficacy will be assessed by comparing the punch biopsy results between the Screening Visit (having had HSIL to qualify for vaccination) and the 12-Month Visit (±2 weeks) (FIG. 8). LEEP will not be performed to assess efficacy, but it will be offered at no cost to subjects who have persistent HSILs at the 12 Mo Visit.

The design of proposed Phase II trial is open-label, single site, and single arm. We plan to use a historical placebo group from a clinical trial with similar design (i.e., enrollment of subjects with biopsy-proven CIN2/3, and clinical response assessed by biopsy in 15 months) for comparison [57]. Among the first 2 dose levels examined in our Phase I clinical trial, the 50 ug dose has demonstrated the best clinical response (4 of 6 or 67% complete response). Since 34 of 117 (29%) of the historical control group demonstrated regression, a sample size of 20 for the vaccine group would give 90% power ($\alpha$=0.05, tails=2). However, the clinical response rate of 67% is based on a small number of subjects. If we conservatively estimate the response rate to be 55%, then a sample size of 53 would be required (90% power, $\alpha$=0.05, tails=2). Accounting for potential screen failures and attrition rate, we plan to screen 110 subjects and to vaccinate 70 subjects for the Phase II clinical trial. While the use of historical placebo group is not as rigorous as having a concurrent placebo group, a concurrent placebo group with biopsy-proven CIN2/3 that would go untreated for 12 months would be difficult to ethically justify.

1.5.10 Rationale for Secondary Outcome Measure: Safety

The combination of HPV peptides and Candin® was first tested in the Phase I clinical trial, and appears to be safe as no vaccine-related AEs>grade 2 have been reported (Table 2). Safety will be assessed in the same manner in the Phase II clinical trial using CTCAE 4.03.

1.5.11 Rationale for Tertiary Outcome Measures: Immunological Response and Viral Clearance 1.5.11.1 Rationale for Measuring HPV-Specific T-Cell Response HPV-specific CD3 T-cell responses will be assessed using immune assay such as the IFN-$\gamma$ ELISPOT assay before vaccination, after 2 vaccinations, and after 4 vaccinations as was done in the Phase I clinical trial (FIG. 8). In order to evaluate the role of CD3 T-cells in vaccine efficacy, whether clinical response and viral clearance can be predicted based on the CD3 T-cell activities will be assessed.

1.5.11.2 Rationale for Measuring Circulating Immune Cells

The level of circulating immune cells, including CD4 T-cells, Th1 cells, Th2 cells, regulatory T-cells (Treg), and myeloid-derived suppressor cells (MDSC), will be assessed before vaccination, after 2 vaccinations, and after 4 vaccinations. Preliminary data from the Phase I clinical trial indicate that PepCan may have decrease Th2 responses resulting in increased effector immune activity (FIG. 9). Whether the levels of these circulating immune cells can be used to predict vaccine efficacy in terms of clinical response and viral clearance will be investigated.

1.5.11.3 Rationale for Measuring Viral Clearance

HPV-DNA testing will be performed at the Screening Visit, 6-Month Visit, and 12-Month Visit (FIG. 10). Thus far, all study participants had at least one HPV type at the Screening Visits. Clearance of at least one HPV type appears to correlate with clinical response. In the Phase II study, an HPV type would be considered to be cleared if it is present at the Screening Visit but not at the 6-Month and 12-Month Visits.

1.5.12 Rationale of Other Outcome Measures: Predict Vaccine Response Using Various Factors Such as Age, HLA Types, HPV Types, Proteomics Profiling, Cytokine/Chemokine Profiling, and Laboratory Tests; Determine Cross-Protection and Examine Epitope Spreading and Cross-Reactivity as Possible Mechanisms Not all vaccine recipients are expected to have clinical response. Some may have persistent HSIL, and some may progress to invasive squamous cell carcinoma. It would be valuable to identify factors that are associated with a favorable response so an educated decision can be made as to who should receive the vaccine, and how long one should wait before opting for surgical treatments. Therefore, a systems biology approach may be employed to determine factors that are associated with clinical response and viral clearance.

The Phase I clinical trial has indicated that PepCan is effective in HSILs with HPV 16 and non-16 HPV types. In the Phase II clinical trial, against which non-16 HPV types it is effective may be determined. Furthermore, epitope spreading and cross-reactivity may be investigated as possible mechanisms behind cross-protection.

2 Objectives

Primary Objective: Efficacy 2.1

To assess the efficacy of PepCan in a Phase II clinical trial by determining clinical response which will be assessed by obtaining colposcopy-guided biopsy at the 12-Month Visit. If, upon the 12-Month visit biopsy, a subject does not have any evidence of CIN 2/3, she would be considered a "responder". Some would have regressed to CIN 1, and others may have no dysplasia. If there is still CIN 2 and/or 3 present at the 12-Month Visit, the subject will be considered a "non-responder".

Secondary Objective: Safety 2.2

Safety will be assessed by documenting AEs from the time of enrollment until the 12-Month Visit according to CTCAE v4.03.

Tertiary Objectives: Immunological Response and Viral Clearance 2.3

Immunological assessment in terms of HPV-specific CD3 T-cell responses will be assessed using an IFN-$\gamma$ ELISPOT assay while circulating levels of CD4, Th1, Th2, Treg, and MDSC cells will be assessed by FACS analysis before vaccination, after 2 vaccinations and after 4 vaccinations. Virological assessments will be made at Screening Visit, 6-Month Visit, and 12-Month Visit.

Other Objectives 2.4

To evaluate predictive factors for response to the vaccine (in order to determine what specific group of women should receive the vaccine and timing of surgical treatments), various parameters such as age, HLA types, HPV types, proteomics profiling, cytokine/chemokine profiling, laboratory results, prophylactic HPV vaccination, tobacco use, oral contraceptive use, Pap smear results, CIN grade (CIN 2 vs. CIN 3), initial vital signs, body mass index, CD3 T-cell response to HPV 16 E6, and circulating immune cells may be analyzed.

Cross-protection in terms of clinical response may be determine by tallying each HPV event detected prior to vaccination in subjects who demonstrate HSIL regression for each of the 36 HPV types (other than 16) tested.

Cross-protection in terms of viral clearance may be determined by tallying each HPV event that is present at Screening Visit but becomes undetectable at both 6-Month and 12-Month Visits for each of the 36 HPV types tested.

Epitope spreading and cross-reactivity may be examined in selected subjects.

3 Investigational Product

Test Article 3.1

3.1.1 HPV Peptides

PepCan will contain four HPV 16 E6 peptides: E6 1-45 (Ac-MHQKRTAMFQDPQER PRKLPQLCTELQTTIH-DIILECVYCKQQLL-NH2 (SEQ ID NO:2)), E6 46-80 (Ac-RREVYDFAFRDLCIV YRDGN PYA VCDKCLKFYSKI-NH2 (SEQ ID NO:3)), E6 81-115 (Ac-SEYRHYCYSLYGTTLEQQYNK PLCDLLIRCINCQK-NH2 (SEQ ID NO:4)), and E6 116-158 (Ac-PLCPEEKQRHLDKKQRFHNIRGRWT GRCMSCCRSSRTRRETQL-NH2 (SEQ ID NO:5)) (U.S.

Pat. No. 8,652,482). Commercially produced cGMP-grade peptides (CPC Scientific, San Jose, Calif.) will be examined.

The four peptides will be provided in a single vial in lyophilized form, and will be stored at −70° C. (acceptable range −65° C. to −75° C.) except during shipping and immediately prior to use.

3.1.2 Candin®

Candida Albicans Skin Test Antigen for Cellular Hypersensitivity will be supplied in the commercially marketed drug Candin®. The vials will be stored at 2° C. to 8° C. as directed by the package insert until use. This product is approved for multi-dosing. The dose of Candin® per injections for this study is 0.3 ml.

3.1.3 Combining HPV Peptides and Candin®

Sterile water will be added to a vial containing the four cGMP peptides on the day of. Appropriate volume of reconstituted peptides will be drawn in a syringe depending on the dose level, and 0.3 ml of Candin® will be drawn into the same syringe. The combined peptide-Candin® mixture should be kept on ice or in refrigerator until immediately before injection.

Treatment Regimen 3.2

Subjects will receive four injections of PepCan (50 to 500 µg/peptide/injection) via intradermal injection in the extremities with three weeks between each injection.

4 Study Design

Overview 4.1

This is a single-arm, open-label, Phase II clinical trial of PepCan to treat women with biopsy-proven HSIL. The study design closely resembles the latest guidelines for treating young women with HSIL [14]. Study participants will be patients attending the UAMS Obstetrics and Gynecology Clinics with untreated biopsy-proven HSILs and patients referred from other clinics. Four injections (one every 3 weeks) of the vaccine will be intradermally administered in the extremities. Clinical response will be assessed by comparison of colposcopy-guided biopsy results obtained prior to vaccination and at 12-Month Visit. Safety will be monitored from the time of enrollment through the 12-Month Visit. Blood will be drawn for laboratory testing and immunological analyses ("blood test") prior to injection, and after the second and fourth vaccination. Blood will be drawn to aid T-cell analyses ("blood draw") after the first and third vaccinations, and possibly at the 6-Month, 12-Month and or Optional LEEP visits. HPV-DNA testing will be performed at Screening and 6- and 12-Month visits (FIG. 10). If a subject has persistent HSIL at the 12-Month Visit or if a subject is exited due to excessive toxicity, she will be given an option to return for a LEEP visit. Alternatively, she may choose to exit the study and be followed by her physician for up to 2 years of observation as recommended before surgical treatment [14].

Monitoring Toxicity 4.2

Serious toxicity will be defined (using CTCAE v 4.03) as drug-related:

Grade II or higher allergic reactions. Grade II is defined as "intervention or infusion interruption indicated; responds promptly to symptomatic treatment (e.g., antihistamines, NSAIDS, narcotics); prophylactic medications indicated for ≤24 hours". Grade III is defined as "prolonged (e.g., not rapidly responsive to symptomatic medication and/or brief interruption of infusion); recurrence of symptoms following initial improvement; hospitalization indicated for clinical sequelae (e.g., renal impairment, pulmonary infiltrates)".

Grade II or higher autoimmune reactions. Grade II is defined as "evidence of autoimmune reaction involving a non-essential organ or function (e.g., hypothyroidism)". Grade III is defined as "autoimmune reactions involving major organ (e.g., colitis, anemia, myocarditis, kidney)".

Any Grade III or higher event.

Any subject who experiences serious toxicity will be discontinued from the study.

Stopping Rules 4.3

The study enrollment and vaccine administration will be suspended if any subject experiences vaccine-related Grade IV or higher AE. These activities can re-start only after the Medical Monitor and applicable regulatory authorities grant permission.

The sponsor may decide to stop the study at any point, for any reason.

5 Subject Enrollment and Study Duration 5.1. Subject Population, Recruitment, and Informed Consent Process Women, aged 18 to 50 years, seen at the UAMS Obstetrics and Gynecology Clinics and ANGELS Telecolposcopy program with recent Pap smear results positive for HSIL or "Cannot rule out HSIL" will be recruited through Physician referral, brochures, flyers, UAMS website, and word of mouth by study team; interested potential subjects will contact the study coordinator to discuss study; coordinator will conduct initial inclusion/exclusion criteria assessment, schedule subject for screening visit, and send a copy of the informed consent document for the subject to review Other women with recent abnormal Pap smear results positive for HSIL or "Cannot rule out HSIL" will be recruited through clinic referral, brochures, flyers (distributed on and off campus), UAMS website, and advertisements in newspaper, radio, and/or social networking site; interested potential subjects will contact the study coordinator to discuss study; coordinator will conduct inclusion/exclusion criteria assessment, schedule subject for screening visit, and send a copy of the informed consent document for the subject to review; coordinator will request that subject obtain copy of Pap smear result from their physician's office and bring with them to the screening visit Women with recent diagnosis (the duration between the day of diagnosis and the day of 1st injection needs to be ≤60 days) of HSIL on colposcopy guided punch biopsy will be recruited through clinic referral, brochures, flyers (distributed on and off campus), UAMS website, and advertisements in newspaper, radio, and/or social networking site; interested potential subjects will contact the study coordinator to discuss study; coordinator will conduct inclusion/exclusion criteria assessment, schedule subject for screening visit, and send a copy of the informed consent document for the subject to review; coordinator will request that subject obtain copies of medical records of abnormal biopsy from their physician's office and bring it with them to the screening visit 5.1.1 Inclusion Criteria Aged 18-50 years Had recent (≤60 days) Pap smear result consistent with HSIL or "cannot rule out HSIL" or HSIL on colposcopy guided biopsy Untreated for HSIL or "Cannot rule out HSIL"

Able to provide informed consent

Willing and able to comply with the requirements of the protocol with a good command of the English language 5.1.2 Exclusion Criteria
  History of disease or treatment causing immunosuppression (e.g., cancer, HIV, organ transplant, autoimmune disease)
  Being pregnant or attempting to be pregnant within the period of study participation
  Breast feeding or planning to breast feed within the period of study participation
  Allergy to *Candida* antigen
  History of severe asthma requiring emergency room visit or hospitalization
  Current use of beta-blocker medication (may not respond to epinephrine in case of anaphylaxis)
  History of invasive squamous cell carcinoma of the cervix
  If in the opinion of the Principal Investigator or other Investigators, it is not in the best interest of the patient to enter this study 5.1.3 Informed Consent Process
  Potential subjects will be provided the informed consent form before the screening visit and allowed as much time needed to make decisions regarding study participation
  The study coordinator/study team member authorized by PI to administer informed consent discussion will discuss the study in detail (including the age-specific standard of care guidelines as periodically released by the American Society of Colposcopy and Cervical Pathology) with the potential subject at any time before the screening visit or at a UAMS Gynecology clinic when she arrives for the screening visit (prior to any study-related procedures), and answer any questions the subject may have about the study; discussions will be conducted in English
  As consent is an ongoing process, subjects will be asked if they still wish to participate in the study prior to study procedures conducted at each study visit Pace of Enrollment 5.2
  During the Phase I study, approximately two thirds of subjects enrolled qualified for vaccination. Taking into account the screen-failure rate and attrition rate (currently about 5% per year), we plan to enroll 110 subjects for screening, and to initiate vaccination in 70 subjects.

Study Duration 5.3
  The study duration will be up to 66 months. Each subject is expected to be in the study for approximately 16 months or longer if LEEP excision is performed.

6 Study Visits
Scheduling Study Visits 6.1
  The Study Coordinator will schedule study visits (Screening, Vaccination, 6-Month, 12-Month, and Optional LEEP Visits) at the UAMS Obstetrics and Gynecology Clinics and the Clinical Research Services Core (CRSC). The Screening, 6-Month, 12-Month, and Optional LEEP Visits are expected to take approximately 90 minutes. However, they may be longer on busy clinic days. Vaccination Visits are expected to take approximately 60 minutes.

Study Visit Windows 6.2
6.2.1 Between Visits of an Individual Subject
  The first vaccination visit (Visit 1) should be scheduled as soon as possible after all results from the screening visit are available, and subjects are deemed qualified to continue to the vaccination phase of the study, but no later than 60 days after the day punch biopsy was obtained (the screening day for most of the subjects).
  The subsequent vaccination/lab visits (Visits 2-5) should be scheduled 3 weeks±7 days apart.
  The 6-Month visit should be scheduled 6 months+2 weeks following Visit 4
  The 12-Month visit should be scheduled 6 months+2 weeks following 6-Month visit
  Optional LEEP visit (if subject chooses) should be scheduled as soon as possible after 12-Month visit or after a subject is exited due to serious toxicity Screening Visit 6.4
6.4.1 Procedures for Screening Visit
  Review inclusion/exclusion criteria
  Obtain informed consent (if not previously obtained)
  Have the subject fill out "Subject Contact Information" (Appendix 2) during the visit
  Have the subject fill out "Screening Visit Questionnaire" (Appendix 3) during the visit
  Obtain demographic information
  Obtain subject's history
    Medical history: Be sure to ask for history of previous abnormal Pap smears and how they were treated
    Drug allergies
    Concomitant medications
  Perform a physical examination
    Obtain vital signs
      Blood pressure (<200/120 mm Hg acceptable)
      Heart rate (50-120 beats per min acceptable)
      Respiratory rate (<25 breaths per min acceptable)
      Temperature (<100.4° F.)
      Weight (no restriction)
  For a subject with child-bearing potential
    Discuss the risks involved in becoming pregnant while receiving vaccine
    Ask which birth-control method she will be using while participating in the vaccine trial; FDA acceptable forms include sterilization, implantable rod, IUD, shot/injection, oral contraceptives, barrier methods (vaginal ring, condom, diaphragm, cervical cap), and emergency contraception
  Perform colposcopy
    Obtain ThinPrep for HPV-DNA testing
    Obtain punch biopsy and endocervical curettage if determined to be necessary by the physician (HSIL needs to be confirmed to be eligible)
    Physician may acquire four-quadrant blind biopsy if no areas of lesions are visible upon colposcopy
    Record the lesion(s), locations on the cervix, image cervix using the colposcope-mounted image capture system (if available), and indicate where biopsy was taken
    Record in how many cervical quadrants the lesions are visible
    If the subject has already been diagnosed with HSIL by biopsy, there is no need to repeat it. However, colposcopy could be repeated to document the location of the lesion(s), and to collect ThinPrep for HPV-DNA testing.
  Draw blood tubes for CBC, hepatic function, and renal function (to be performed in UAMS clinical laboratory)

Vaccination Visits (Visits 1-5) 6.5
6.5.1 Procedures for Visit 1
  Ask if any medications have been started or stopped since the last visit
  Urine pregnancy test prior to vaccination
  Measure height and weight to determine BMI
  Take vital signs prior to injection
  Blood will be drawn for
    Immunomonitoring and other analyses (six to eight 10.0 ml rubber green top sodium heparin tubes)

CBC (one 3.0 ml purple top EDTA tube; to be performed in UAMS clinical laboratory)
Hepatic and renal panels (two 4.5 ml light green top lithium heparin tubes; to be performed in UAMS clinical laboratory)
Administer vaccination injection
Repeat vital signs after at least 30 min has passed since the injection
Monitor for any immediate adverse reactions
Offer dose of ibuprofen or naproxen
Hand out "Subject Diary" (Appendix 4) and ask the subject to fill it out and bring it back at the next visit 6.5.2 Procedures for Visit 2
Ask for the filled out "Subject Diary". If the subject did not return it, ask "Have you experienced any side effects since the last injection?"
Ask if any medications have been started or stopped since the last visit
Urine pregnancy test prior to vaccination
Take vital signs prior to injection
Blood will be drawn for
Immunomonitoring and other analyses (six to eight 10.0 ml rubber green top sodium heparin tubes)
Administer vaccination injection
Repeat vital signs after at least 30 min has passed since the injection
Monitor for any immediate adverse reactions
Offer dose of ibuprofen or naproxen
Hand out "Subject Diary" (Appendix 4) and ask the subject to fill it out and bring it back at the next visit 6.5.3 Procedures for Visit 3
Ask for the filled out "Subject Diary". If the subject did not return it, ask "Have you experienced any side effects since the last injection?"
Ask if any medications have been started or stopped since the last visit
Urine pregnancy test prior to vaccination
Take vital signs prior to injection
Blood will be drawn for
Immunomonitoring and other analyses (six to eight 10.0 ml rubber green top sodium heparin tubes)
CBC (one 3.0 ml purple top EDTA tube; to be performed in UAMS clinical laboratory)
Hepatic and renal panels (two 4.5 ml light green top lithium heparin tubes; to be performed in UAMS clinical laboratory)
Administer vaccination injection
Repeat vital signs after at least 30 min has passed since the injection
Offer dose of ibuprofen or naproxen
Monitor for any immediate adverse reactions
Hand out "Subject Diary" (Appendix 4) and ask the subject to fill it out and bring it back at the next visit 6.5.4 Procedures for Visit 4
Ask for the filled out "Subject Diary". If the subject did not return it, ask "Have you experienced any side effects since the last injection?"
Ask if any medications have been started or stopped since the last visit
Urine pregnancy test prior to vaccination
Take vital signs prior to injection
Blood will be drawn for
Immunomonitoring and other analyses (six to eight 10.0 ml rubber green top sodium heparin tubes)
Administer vaccination injection
Repeat vital signs after at least 30 min has passed since the injection
Monitor for any immediate adverse reactions
Offer dose of ibuprofen or naproxen
Hand out "Subject Diary" (Appendix 4) and ask the subject to fill it out and bring it back at the next visit 6.5.5 Procedures for Visit 5
Ask for the filled out "Subject Diary". If the subject did not return it, ask "Have you experienced any side effects since the last injection?"
Blood will be drawn for
Immunomonitoring and other analyses (six to eight 10.0 ml rubber green top sodium heparin tubes)
CBC (one 3.0 ml purple top EDTA tube)
Hepatic and renal panels (two 4.5 ml light green top lithium heparin tubes)

6-Month Visit 6.6
The 6-Month visit will be scheduled approximately six months (±2 weeks) after Vaccination Visit 4.
6.6.1 Procedures for 6-Month Visit
Ask if any medications have been started or stopped since last visit
Perform colposcopy
Obtain ThinPrep for HPV-DNA testing
Record the lesion(s), locations on the cervix, image cervix using the colposcope-mounted image capture system (if available)
Record in how many cervical quadrants the lesions are visible
If determined to be necessary by the physician (ONLY in cases where there is a suspicion of progressive disease), obtain punch biopsy and endocervical curettage
Based on the results of the ELISPOT assay, some subjects will be further studied for cross-reactivity, epitope spreading and/or defining novel T-cell epitopes, and blood will be drawn
Six to eight 10.0 ml rubber green top sodium heparin tubes 12-Month Visit 6.7
The 12-Month visit will be scheduled approximately six months (±2 weeks) after the 6-Month visit.
6.7.1 Procedures for 12 Month Visit
Perform a physical examination
Obtain vital signs
Blood pressure
Heart rate
Respiratory rate
Temperature
Weight
Ask if any medications have been started or stopped since last visit
Perform colposcopy
Obtain ThinPrep for HPV-DNA testing
Record the lesion(s), locations on the cervix, image cervix using the colposcope-mounted image capture system (if available)
Record in how many cervical quadrants the lesions are visible
Obtain punch biopsy and possibly endocervical curettage
If determined to be necessary by the physician, perform endocervical curettage
Blood may be drawn from some subjects as explained above for
Immunomonitoring and other analyses (six to eight 10.0 ml rubber green top sodium heparin tubes)
Have the subject fill out "12 Month Visit Questionnaire" (Appendix 7) during the visit

6.7.2 Follow-Up to the 12 Month Visit

The Study Coordinator and Principal Investigator or Co-Investigator will review all information and test results from the 12 Month Visit. If no evidence of HSIL upon biopsy, the subject will complete the study. If persistent HSIL is present, the subject may choose either to (1) be followed by her private gynecologist for another one year prior to LEEP or (2) to have LEEP performed as a part of the study.

Optional LEEP Visit 6.8
6.8.1 Procedures for LEEP Visit

Blood may be drawn from some subjects as explained above for
  Immunomonitoring and other analyses (six to eight 10.0 ml rubber green top sodium heparin tubes)
Perform LEEP biopsy
  Obtain ThinPrep specimen for HPV-DNA testing
  Excise visible lesion or, if no visible lesion seen, excise from an area where biopsy was obtained at the 12-Month Visit

8 Outcome Measures

Clinical Assessments (UAMS Pathology Laboratory) 8.1

Clinical response will be assessed (by Pathologists on service in the Pathology Department) by comparing punch biopsy results from screening (having had HSIL is the inclusion criterion) with the punch biopsy performed at the 12 Month visit. The subject will be considered a "responder" if the 12 Month biopsy is negative for HSIL (no evidence of CIN 2/3), or a "non-responder" if the biopsy shows HSIL (CIN 2 and/or 3).

Virological Study-HPV-DNA Testing (Nakagawa Laboratory) 8.2

The ThinPrep samples will be tested for the presence of HPV-DNA. A commercially available kit such as the "Linear Array HPV Genotyping Test" may be used (Roche Molecular Diagnostics, Inc., Alameda, Calif.). This kit tests for 37 HPV types (6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73, 81, 82, 83, 84, IS39, and CP6108). The human beta-globin signal will also be assayed as a positive control for sample adequacy for DNA content from each sample. Positive-control samples (with added HPV plasmid DNA and plasmid-encoded human beta-globin gene) and negative-control samples (no HPV plasmid DNA and no human beta-globin gene) are provided by the manufacturer and will be included in each experiment. HPV types 31, 33, 35, 52, 58, and 67 will be considered "HPV 16-Related", additionally HPV types 18, 39, 45, 51, 53, 56, 59, 66, 68, 69, 70, 73, and 82 will be considered "High Risk", and types 6, 11, 40, 42, 54, 61, 62, 71, 72, 81, 83, 84, and CP6108 will be considered "Low Risk" [58].

The virological response will be assessed by comparing HPV-DNA testing results before and after vaccination. The subject will be considered a "clearer" if at least one HPV type(s) present before vaccination becomes undetectable at both 6-Month and 12-Month Visits. Otherwise, a subject will be considered a "persistor" as long as at least one HPV type was detected at baseline.

Immunological Assessments 8.3
8.3.1 ELISPOT Assay (Nakagawa Laboratory)

An immune assay such as an ELISPOT assay to assess the presence of HPV-specific T-cells will be performed. After each blood draw, PBMCs will be separated into CD14+ and CD14-populations and cryopreserved. To eliminate interassay variability, all three blood samples (before vaccination, after two vaccinations, and after four vaccinations) will be used to establish T-cell lines and to perform ELISPOT assays. CD3 T-cell lines will be established by stimulating in vitro magnetically selected CD3 cells with autologous mature dendritic cells exposed to HPV 16 E6-vac, E7-vac, E6-GST, and E7-GST. ELISPOT assays will be performed as previously described [28]. We typically examine 16 regions within the HPV 16 E6 and E7 proteins (E6 1-25, E6 16-40, E6 31-55, E6 46-70, E6 61-85, E6 76-100, E6 91-115, E6 106-130, E6 121-145, E6 136-158, E7 1-25, E7 16-40, E7 31-55, E7 46-70, E7 61-85, and E7 76-98). The assay will be performed in triplicate if sufficient cells are available. In order to compare each region before vaccination and after 2 or 4 injections, a t test for paired samples will be performed, as described previously [59]. Therefore, each subject will be assessed in terms of the number of regions with statistically significant increased T-cell responses after two injections or four injections determined by using Student's paired t-test. Remaining CD3 T-cells may be used to assess the recognition of homologous epitopes from other high-risk HPV types, to describe novel epitopes, and/or to assess the endogenous processing of such epitopes.

8.3.2 Measuring Immune Cells
8.3.2.1 Circulating Immune Cells (Nakagawa Laboratory)

A small amount of PBMCs (approximately $3 \times 10^6$ cells) from blood draws at Visit 1, Visit 3, and Visit 5 will also be used to monitor levels of circulating immune cells such as Tregs and MDSC to assess whether vaccination may decrease their levels [60]. Flow cytometry will be used to determine the number of CD4+CD25+FOXP3+(Treg) and CD14+HLA-DR−/low (MDSC) cells [29, 61]. Tbet (Th1), GATA3 (Th2), and/or ROR gammaT (TH17) positive cells may also be examined. The number of circulating immune cells will be determined before vaccination, after two, and after four injections.

8.3.2.2 Cervical Immune Cells (UAMS Experimental Pathology Core)

After routine pathological diagnosis has been made from LEEP sample obtained at the Optional LEEP Visit, additional sections may be examined for cervical immune cells such as those positive for CD3 (T-cell), CD4 (helper T-cell), CD8 (cytotoxic T-cell), CD56 (NK cell), CD1a (Langerhan cells important in antigen presentation), CD20 (B-cell), CD68 (macrophage), FOXP3 (Treg), Tbet (Th1), and Mad-CAM-1 (addressing involved with T-cell infiltration). Eosinophils (Th2) may also be examined.

8.3.3 Others

Additional analyses that may be performed using blood samples to assess vaccine response include antibody production to HPV proteins, cytokine responses (Nakagawa laboratory), and changes in protein expression (UAMS Proteomics Core Laboratory).

9 Data Analysis

Assessing Efficacy 9.1

A historical placebo group, from a previously reported study with a similar study design (i.e., enrollment of subjects with biopsy-proven CIN2/3, and clinical response assessed by biopsy in 15 months), will be used for comparison [57]. The response rate in vaccine recipients who completed the trial (estimated to be 50 to 60 subjects) will be compared with that of the historical placebo group which was 29% (34 of 117) using Fisher's exact test. See "Rationale for Primary Outcome Measure: Efficacy" (Section 1.5.9) for power analysis and sample size justification.

Assessing Safety: Summary of Adverse Events 9.2

Subjects who received at least one dose of the vaccine will be included in safety assessments. Results will be tabulated as shown in Table 3. The type of adverse reactions, the CTCAE grades, and whether the reactions are vaccine-related will be indicated.

Assessing Immunological Response and Viral Clearance 9.3
9.3.1 Immunological Response
9.3.1.1 CD3 T-Cell Response to HPV As described above, a paired t-test for paired samples will be performed in order to compare each region before vaccination and after 2 or 4 injections, as shown in FIG. 8.

A correlation between CD3 T-cell response to HPV and clinical response will be examined by drawing a contingency table for a number of subjects with at least one region with statistically significant increase to E6 in "responders" and "non-responders". Fisher's exact test will be used.

9.3.1.2 Circulating Immune Cells

The changes in percentage of circulating immune cells such as CD4, Th1, Th2, Treg, and MDSC will be compared after 2, and 4 vaccinations with baseline as shown in FIG. 9. Paired t-test and one-way ANOVA will be performed to determine statistical significance.

A correlation between circulating immune cells and clinical response will be examined. The changes in the percentages of circulating immune cells between pre-vaccination samples and post 4 injection samples will be compared between the "responders" and the "non-responders".

9.3.2 Viral Clearance

HPV-DNA testing will performed using Thin-Prep samples from Screening, 6-Month, and 12-Month Visits.

A correlation between CD3 T-cell response to HPV and virological response will be examining by drawing a contingency table for a number of subjects with at least one region with statistically significant increase to E6 in "clearers" and "persistors". Fisher's exact test will be used.

A correlation between circulating immune cells and viral clearance will be examined. The changes in the percentages of circulating immune cells between pre-vaccination samples and post 4 injection samples will be compared between the "clearers" and the "persistors".

Factors Contributing to Study Recruitment and Retention 9.4

Based on data provided in "Screening Visit Questionnaire", "Early Termination Questionnaire", and "12 Month Visit Questionnaire", factors that contribute to subject recruitment and retention may be assessed. The Fisher's exact test will be used to compare factors such as frequent use of Facebook private group, motivation for entering the study, or having young children will be compared between the subjects who exited the study early and the subjects who completed the study.

Factors Predicting Clinical Response and Viral Clearance 9.5

Because proteomics data will be collected at 3 time points, we will identify clusters of proteins which are associated with specific dynamic responses to vaccine (e.g. increasing, decreasing, U-shaped) and also identify protein-expression signatures which predict vaccine response. Protein clustering will be performed using Mfuzz[62], a noise-robust clustering method originally developed for gene expression microarray time-course data, but which has been successfully applied to proteomics data[63]. We will test protein clusters for enrichment of specific gene ontology (GO) annotations to elucidate underlying causes of differential response to vaccine. In addition to proteomics data, we will test other variables for prediction of vaccine response, first by univariate analyses, and then multivariable analysis with variable selection using lasso[64] with ten-fold cross validation. Computations will be performed in the R and R/Bioconductor[65] environments. Variable selection using lasso will be implemented with the package glm-mLasso, while enrichment analysis for Gene Ontology terms will be performed using topGO.

Definitions 10.1
10.1.1 Adverse Event

An adverse event is any occurrence or worsening of an undesirable or unintended sign, symptom, or disease that is temporally associated with the use of the vaccine, and it will be graded according to the Common Terminology Criteria for Adverse Events (CTCAE) Version 4.03. Local and/or systemic adverse events may include itching, burning, pain, peeling, rash, oozing, redness, tenderness, scarring, fever, nausea, dizziness, and wheezing. The subjects will be allowed to use and provided analgesics (such as ibuprofen or naproxen) according to the appropriate dosages after injections to limit any adverse events that may occur. Any adverse event will be reviewed and considered related or not related to the vaccine. All applicable events will be reported to the IRB according to IRB policy 10.2 and the FDA according to 21 CFR 312.32.

10.1.2 Serious Adverse Event

A serious adverse event is any medical event that
Results in death
Is an immediate threat to life
Requires hospitalization or prolongation of existing hospitalization
Is a congenital anomaly or birth defect, or
Other important medical events that have not resulted in death, are not life-threatening, or do not require hospitalization, may be considered serious adverse events when, based upon the appropriate medical judgment, they are considered to jeopardize the subject and may require medical or surgical intervention to prevent one of the outcomes listed above.

REFERENCES FOR EXAMPLE 4

[1] Cancer Facts & Figures. American Cancer Society; 2012.
[2] Crum C. Robbins & Cotran Pathologic Basis of Disease. 7th Edition ed. Philadelphia London Toronto Montreal Sydney Tokyo: W. B. Saunders Co., 2004.
[3] Munoz N, Bosch F X, de Sanjose S, Herrero R, Castellsague X, Shah K V, Snijders P J, Meijer C J. Epidemiologic classification of human papillomavirus types associated with cervical cancer. N Engl J Med. 2003; 348:518-27.
[4] Beaudenon S, Kremsdorf D, Croissant O, Jablonska S, Wain-Hobson S, Orth G. A novel type of human papillomavirus associated with genital neoplasias. Nature. 1986; 321:246-9.
[5] Crum C P, Mitao M, Levine R U, Silverstein S. Cervical papillomaviruses segregate within morphologically distinct precancerous lesions. J Virol. 1985; 54:675-81.
[6] Reid R. Human papillomaviral infection. The key to rational triage of cervical neoplasia. Obstet Gynecol Clin North Am. 1987; 14:407-29.
[7] Lorincz A T, Lancaster W, Temple G. Cloning and characterization of the DNA of a new human papillomavirus from a woman with dysplasia of the uterine cervix. J Virol. 1986; 58:225-9.
[8] Lorincz A T, Quinn A, Lancaster W, Temple G F. A new type of papillomavirus associated with cancer of the uterine cervix. Virology. 1987; 159:187-190.
[9] Fuchs P G, Girardi F, Pfister H. Human papillomavirus DNA in normal, metaplastic, preneoplastic and neoplastic epithelia of the cervix uteri. Int J Cancer. 1988; 41:41-5.
[10] Kiviat N B, Koutsky L A, Critchlow C W, Lorincz A T, Cullen A P, Brockway J, Holmes K K. Prevalence and cytologic manifestations of human papilloma virus (HPV) types 6, 11, 16, 18, 31, 33, 35, 42, 43, 44, 45, 51, 52, and 56 among 500 consecutive women. Int J Gynecol Pathol. 1992; 11:197-203.

[11] Richart R M, Barron B A. A follow-up study of patients with cervical dysplasia. Am J Obstet Gynecol. 1969; 105:386-93.

[12] Nash J D, Burke T W, Hoskins W J. Biologic course of cervical human papillomavirus infection. Obstet Gynecol. 1987; 69:160-2.

[13] Campion M J, McCance D J, Cuzick J, Singer A. Progressive potential of mild cervical atypia: prospective cytological, colposcopic, and virological study. Lancet. 1986; 2:237-40.

[14] Massad L S, Einstein M H, Huh W K, Katki H A, Kinney W K, Schiffman M, Solomon D, Wentzensen N, Lawson H W. 2012 updated consensus guidelines for the management of abnormal cervical cancer screening tests and cancer precursors. Obstet Gynecol. 2013; 121:829-46.

[15] Bruinsma F J, Quinn M A. The risk of preterm birth following treatment for precancerous changes in the cervix: a systematic review and meta-analysis. BJOG. 2011; 118:1031-41.

[16] Nieminen P, Harper D M, Einstein M H, Garcia F, Donders G, Huh W, Wright T C, Stoler M, Ferenczy A, Rutman O, Shikhman A, Leung M, Clinch B, Calleja E. Efficacy and safety of RO5217990 treatment in patients with high grade cervical intraepithelial neoplasia (CIN2/3). 28th International Papillomavirus Conference. Puerto Rico2012.

[17] Daayana S, Elkord E, Winters U, Pawlita M, Roden R, Stern P L, Kitchener H C. Phase II trial of imiquimod and HPV therapeutic vaccination in patients with vulval intraepithelial neoplasia. Br J Cancer. 2010; 102:1129-36.

[18] Kenter G G, Welters M J, Valentijn A R, Lowik M J, Berends-van der Meer D M, Vloon A P, Essahsah F, Fathers L M, Offringa R, Drijfhout J W, Wafelman A R, Oostendorp J, Fleuren G J, van der Burg S H, Melief C J. Vaccination against HPV-16 oncoproteins for vulvar intraepithelial neoplasia. N Engl J Med. 2009; 361:1838-47.

[19] Stanley M, Pinto L A, Trimble C. Human papillomavirus vaccines—immune responses. Vaccine. 2012; 30 Suppl 5:F83-7.

[20] Moscicki A B, Palefsky J M, Gonzales J, Smith G, Schoolnik G K. Colposcopic and histologic findings and human papillomavirus (HPV) DNA test variability in young women positive for HPV DNA. J Infect Dis. 1992; 166:951-7.

[21] Moscicki A B, Palefsky J, Smith G, Siboski S, Schoolnik G. Variability of human papillomavirus DNA testing in a longitudinal cohort of young women. Obstet Gynecol. 1993; 82:578-85.

[22] Moscicki A B, Shiboski S, Broering J, Powell K, Clayton L, Jay N, Darragh T M, Brescia R, Kanowitz S, Miller S B, Stone J, Hanson E, Palefsky J. The natural history of human papillomavirus infection as measured by repeated DNA testing in adolescent and young women. J Pediatr. 1998; 132:277-84.

[23] Nakagawa M, Stites D P, Farhat S, Sisler J R, Moss B, Kong F, Moscicki A B, Palefsky J M. Cytotoxic T lymphocyte responses to E6 and E7 proteins of human papillomavirus type 16: relationship to cervical intraepithelial neoplasia. J Infect Dis. 1997; 175:927-31.

[24] Nakagawa M, Stites D P, Palefsky J M, Kneass Z, Moscicki A B. CD4-Positive and CD8-positive cytotoxic T lymphocytes contribute to human papillomavirus type 16 E6 and E7 responses. Clin Diagn Lab Immunol. 1999; 6:494-8.

[25] Nakagawa M, Stites D P, Patel S, Farhat S, Scott M, Hills N K, Palefsky J M, Moscicki A B. Persistence of human papillomavirus type 16 infection is associated with lack of cytotoxic T lymphocyte response to the E6 antigens. J Infect Dis. 2000; 182:595-8.

[26] Farhat S, Nakagawa M, Moscicki A-B. Cell-mediated immune responses to human papillomavirus 16 E6 and E7 antigens as measured by interferon gamma enzyme-linked immunospot in women with cleared or persistent human papillomavirus infection. International Journal of Gynecological Cancer. 2009; 19:508-12.

[27] Nakagawa M, Gupta S K, Coleman H N, Sellers M A, Banken J A, Greenfield W W. A favorable clinical trend is associated with CD8 T-cell immune responses to the human papillomavirus type 16 e6 antigens in women being studied for abnormal pap smear results. J Low Genit Tract Dis. 2010; 14:124-9.

[28] Nakagawa M, Kim K H, Moscicki A B. Patterns of CD8 T-cell epitopes within the human papillomavirus type 16 (HPV 16) E6 protein among young women whose HPV 16 infection has become undetectable. Clin Diagn Lab Immunol. 2005; 12:1003-5.

[29] Kim K H, Greenfield W W, Cannon M J, Coleman H N, Spencer H J, Nakagawa M. CD4+ T-cell response against human papillomavirus type 16 E6 protein is associated with a favorable clinical trend. Cancer Immunol Immunother. 2012; 61:63-70.

[30] Wang X, Coleman H N, Nagarajan U, Spencer H J, Nakagawa M. *Candida* skin test reagent as a novel adjuvant for a human papillomavirus peptide-based therapeutic vaccine. Vaccine. 2013; 31:5806-13.

[31] Audran R, Cachat M, Lurati F, Soe S, Leroy O, Corradin G, Druilhe P, Spertini F. Phase I malaria vaccine trial with a long synthetic peptide derived from the merozoite surface protein 3 antigen. Infect Immun. 2005; 73:8017-26.

[32] Celis E. Overlapping human leukocyte antigen class I/II binding peptide vaccine for the treatment of patients with stage IV melanoma: evidence of systemic immune dysfunction. Cancer. 2007; 110:203-14.

[33] Elliott S L, Suhrbier A, Miles J J, Lawrence G, Pye S J, Le T T, Rosenstengel A, Nguyen T, Allworth A, Burrows S R, Cox J, Pye D, Moss D J, Bharadwaj M. Phase I trial of a CD8+ T-cell peptide epitope-based vaccine for infectious mononucleosis. J Virol. 2008; 82:1448-57.

[34] Hueman M T, Dehqanzada Z A, Novak T E, Gurney J M, Woll M M, Ryan G B, Storrer C E, Fisher C, McLeod D G, Ioannides C G, Ponniah S, Peoples G E. Phase I clinical trial of a HER-2/neu peptide (E75) vaccine for the prevention of prostate-specific antigen recurrence in high-risk prostate cancer patients. Clin Cancer Res. 2005; 11:7470-9.

[35] Kenter G G, Welters M J, Valentijn A R, Lowik M J, Berends-van der Meer D M, Vloon A P, Drijfhout J W, Wafelman A R, Oostendorp J, Fleuren G J, Offringa R, van der Burg S H, Melief C J. Phase I immunotherapeutic trial with long peptides spanning the E6 and E7 sequences of high-risk human papillomavirus 16 in end-stage cervical cancer patients shows low toxicity and robust immunogenicity. Clin Cancer Res. 2008; 14:169-77.

[36] Muderspach L, Wilczynski S, Roman L, Bade L, Felix J, Small L A, Kast W M, Fascio G, Marty V, Weber J. A phase I trial of a human papillomavirus (HPV) peptide vaccine for women with high-grade cervical and vulvar intraepithelial neoplasia who are HPV 16 positive. Clin Cancer Res. 2000; 6:3406-16.

[37] Roberts J D, Niedzwiecki D, Carson W E, Chapman P B, Gajewski T F, Ernstoff M S, Hodi F S, Shea C, Leong S P, Johnson J, Zhang D, Houghton A, Haluska F G. Phase 2 study of the g209-2M melanoma peptide vaccine and low-dose interleukin-2 in advanced melanoma: Cancer and Leukemia Group B 509901. J Immunother. 2006; 29:95-101.

[38] Suekane S, Nishitani M, Noguchi M, Komohara Y, Kokubu T, Naitoh M, Honma S, Yamada A, Itoh K, Matsuoka K, Kanayama H. Phase I trial of personalized peptide vaccination for cytokine-refractory metastatic renal cell carcinoma patients. Cancer Sci. 2007; 98:1965-8.

[39] Gupta R K. Aluminum compounds as vaccine adjuvants. Adv Drug Deliv Rev. 1998; 32:155-72.

[40] Esch R E, Buckley C E, 3rd. A novel *Candida albicans* skin test antigen: efficacy and safety in man. J Biol Stand. 1988; 16:33-43.

[41] Clifton M M, Johnson S M, Roberson P K, Kincannon J, Horn T D. Immunotherapy for recalcitrant warts in children using intralesional mumps or *Candida* antigens. Pediatr Dermatol. 2003; 20:268-71.

[42] Horn T D, Johnson S M, Helm R M, Roberson P K. Intralesional immunotherapy of warts with mumps, *Candida*, and *Trichophyton* skin test antigens: a single-blinded, randomized, and controlled trial. Arch Dermatol. 2005; 141:589-94.

[43] Johnson S M, Horn T D. Intralesional immunotherapy for warts using a combination of skin test antigens: a safe and effective therapy. J Drugs Dermatol. 2004; 3:263-5.

[44] Johnson S M, Roberson P K, Horn T D. Intralesional injection of mumps or *Candida* skin test antigens: a novel immunotherapy for warts. Arch Dermatol. 2001; 137:451-5.

[45] Phillips R C, Ruhl T S, Pfenninger J L, Garber M R. Treatment of warts with *Candida* antigen injection. Arch Dermatol. 2000; 136:1274-5.

[46] Maronn M, Salm C, Lyon V, Galbraith S. One-year experience with *candida* antigen immunotherapy for warts and molluscum. Pediatr Dermatol. 2008; 25:189-92.

[47] Kim K H, Horn T D, Pharis J, Kincannon J, Jones R, O'Bryan K, Myers J, Nakagawa M. Phase 1 clinical trial of intralesional injection of *Candida* antigen for the treatment of warts. Arch Dermatol. 2010; 146:1431-3.

[48] Nakagawa M, Coleman H N, Wang X, Daniels J, Sikes J, Nagarajan U M. IL-12 secretion by Langerhans cells stimulated with *Candida* skin test reagent is mediated by dectin-1 in some healthy individuals. Cytokine. 2014; 65:202-9.

[49] Peng S, Ji H, Trimble C, He L, Tsai Y C, Yeatermeyer J, Boyd D A, Hung C F, Wu T C. Development of a DNA vaccine targeting human papillomavirus type 16 oncoprotein E6. J Virol. 2004; 78:8468-76.

[50] Abbas A K, Lichtman A H, Pillai S. Cellular and Molecular Immunology. 7th ed. Philadelphia: Elsevier, 2011.

[51] Hildesheim A, Herrero R. Effect of a HPV-16/18 vaccine on resolution of infections in women with pre-existing HPV. 23rd International Papillomavirus Conference & Clinical Workshop. Prague, Czech Republic 2006: 6.

[52] Ault K A. Effect of prophylactic human papillomavirus L1 virus-like-particle vaccine on risk of cervical intraepithelial neoplasia grade 2, grade 3, and adenocarcinoma in situ: a combined analysis of four randomised clinical trials. Lancet. 2007; 369:1861-8.

[53] Pedersen C, Petaja T, Strauss G, Rumke H C, Poder A, Richardus J H, Spiessens B, Descamps D, Hardt K, Lehtinen M, Dubin G. Immunization of early adolescent females with human papillomavirus type 16 and 18 L1 virus-like particle vaccine containing AS04 adjuvant. J Adolesc Health. 2007; 40:564-71.

[54] Jemal A, Simard E P, Dorell C, Noone A M, Markowitz L E, Kohler B, Eheman C, Saraiya M, Bandi P, Saslow D, Cronin K A, Watson M, Schiffman M, Henley S J, Schymura M J, Anderson R N, Yankey D, Edwards B K. Annual Report to the Nation on the Status of Cancer, 1975-2009, featuring the burden and trends in human papillomavirus(HPV)-associated cancers and HPV vaccination coverage levels. J Natl Cancer Inst. 2013; 105: 175-201.

[55] Horn T, Johnson S, Roberson P. Intralesional immunotherapy of warts with mumps, *Candida* and *trichophyton* skin test antigens: a single-blinded, randomized and controlled trial. Archives of Dermatology. 2005.

[56] Kenter G, Welters M J, Valentijn A R, Lowik M J, Berends-van der Meer D M, Vloon A P, Offringa R, Drijfhout J W, Wafelman A R, Oostendorp J, Fleuren G J, van der Burg S H, Melief C J. Vaccination against HPV-16 Oncoproteins for Vulvar Intraepitheial Neoplasia. N Engl J Med. 2009; 361:1838-47.

[57] Meyskens F L, Jr., Surwit E, Moon T E, Childers J M, Davis J R, Dorr R T, Johnson C S, Alberts D S. Enhancement of regression of cervical intraepithelial neoplasia II (moderate dysplasia) with topically applied all-trans-retinoic acid: a randomized trial. J Natl Cancer Inst. 1994; 86:539-43.

[58] de Villiers E M, Fauquet C, Broker T R, Bernard H U, zur Hausen H. Classification of papillomaviruses. Virology. 2004; 324:17-27.

[59] Kim K H, Greenfield W, Shotts E, Nakagawa M. Detection of human papillomavirus type 16-specific T lymphocytes by a recombinant vaccinia virus-based enzyme-linked immunospot assay. Clin Vaccine Immunol. 2007; 14:362-8.

[60] Pasare C, Medzhitov R. Toll pathway-dependent blockade of CD4+CD25+ T cell-mediated suppression by dendritic cells. Science. 2003; 299:1033-6.

[61] Greten T F, Manns M P, Korangy F. Myeloid derived suppressor cells in human diseases. Int Immunopharmacol. 2011; 11:802-7.

[62] Futschik M E, Carlisle B. Noise-robust soft clustering of gene expression time-course data. J Bioinform Comput Biol. 2005; 3:965-88.

[63] Krahmer N, Hilger M, Kory N, Wilfling F, Stoehr G, Mann M, Farese R V, Jr., Walther T C. Protein correlation profiles identify lipid droplet proteins with high confidence. Mol Cell Proteomics. 2013; 12:1115-26.

[64] Tibshirani R. Shrinkage and selection via the Lasso. Journal of the Reoyal Statistical Society Series B. 1996; 58:267-88.

[65] Gentleman R C, Carey V J, Bates D M, Bolstad B, Dettling M, Dudoit S, Ellis B, Gautier L, Ge Y, Gentry J, Hornik K, Hothorn T, Huber W, Iacus S, Irizarry R, Leisch F, Li C, Maechler M, Rossini A J, Sawitzki G, Smith C, Smyth G, Tierney L, Yang J Y, Zhang J. Bioconductor: open software development for computational biology and bioinformatics. Genome Biol. 2004; 5:R80.

All publications, patents, and patent documents cited are hereby incorporated by reference.

What is claimed is:

1. A method to solubilize an HPV E6 peptide comprising: solubilizing an HPV E6 peptide A of 20 to 100 amino acids in length and comprising at least 20 consecutive residues of HPV E6 81-115 (residues 81-115 of SEQ ID NO:1) in a buffer that, before the step of solubilizing the HPV peptide A, contains in fully dissolved form two or more HPV peptides Y of 10 to 100 amino acids in length each that collectively comprise at least 50% of the sequence of HPV E6 1-80 (residues 1-80 of SEQ ID NO:1) and at least 50% of HPV E6 116-158 (residues 116-158 of SEQ ID NO:1) to create a final soluble composition containing the peptide A in fully dissolved form and the peptides Y in fully dissolved form.

2. The method of claim 1 wherein the peptide A is acetylated at its amino terminus and amidated at its carboxyl terminus.

3. The method of claim 1 wherein the HPV peptide A comprises residues 81-115 of SEQ ID NO:1.

4. The method of claim 1 wherein the HPV peptide A consists of residues 81-115 of SEQ ID NO:1.

5. The method of claim 4 wherein the peptide A is acetylated on its amino terminus and amidated on its carboxyl terminus.

6. The method of claim 1 wherein the buffer is at a pH of from about pH 3.0 to pH 5.0.

7. The method of claim 6 wherein the buffer comprises at least 2 mM glutamate.

8. The method of claim 1 wherein the peptides A and Y collectively comprise all of SEQ ID NO:1.

9. The method of claim 1 wherein peptide A consists of residues 81-115 of SEQ ID NO:1 and the peptides Y are three peptides consisting of residues 1-45, 46-80, and 116-158 of SEQ ID NO:1.

10. The method of claim 9 wherein each of the peptides A and Y is acetylated on its amino terminus and amidated on its carboxyl terminus, wherein the buffer is at a pH of from about pH 3.0 to pH 5.0, and after solubilization, peptide A and each of the three peptides Y is at 0.1 to 20 mg/ml concentration.

11. The method of claim 1 wherein each of the peptides Y is at at least 80% of the weight-to-volume concentration of peptide A in the final soluble composition.

12. The method of claim 1 wherein peptide A and each of the peptides Y is at 0.1 to 5 mg/ml in the final soluble composition.

13. A pharmaceutical composition comprising:
an HPV E6 peptide A and one or more HPV peptides Y, the composition made by a method comprising:
solubilizing an HPV E6 peptide A of 20 to 100 amino acids in length and comprising at least 20 consecutive residues of HPV E6 81-115 (residues 81-115 of SEQ ID NO: 1) in a buffer that before the step of solubilizing the HPV peptide A, contains in fully dissolved form two or more HPV peptides Y of 10 to 100 amino acids in length each that collectively comprise at least 50% of the sequence of HPV E6 1-80 (residues 1-80 of SEQ ID NO: 1) and at least 50% of HPV E6 116-158 (residues 116-158 of SEQ ID NO:I) to create a final soluble composition containing the peptide A in fully dissolved form and the peptides Y in fully dissolved form.

14. The pharmaceutical composition of claim 13 further comprising a recall antigen.

15. The pharmaceutical composition of claim 13 wherein peptide A consists of residues 81-115 of SEQ ID NO:1 and the peptides Y are three peptides consisting of residues 1-45, 46-80, and 116-158 of SEQ ID NO:1; wherein each of the peptides A and Y is acetylated on its amino terminus and amidated on its carboxyl terminus, wherein the buffer is at a pH of from about pH 3.0 to pH 5.0, and after solubilization, peptide A and each of the three peptides Y is at 0.1 to 20 mg/ml concentration.

* * * * *